(12) United States Patent
Hartmann et al.

(10) Patent No.: US 8,737,708 B2
(45) Date of Patent: May 27, 2014

(54) SYSTEM AND METHOD FOR AUTOMATIC REGISTRATION BETWEEN AN IMAGE AND A SUBJECT

(75) Inventors: Steven L. Hartmann, Superior, CO (US); Bradley A. Jascob, Broomfield, CO (US); Brandon Merkl, Erie, CO (US); Matthew F. Dicorleto, Boulder, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 213 days.

(21) Appl. No.: 13/449,475

(22) Filed: Apr. 18, 2012

(65) Prior Publication Data

US 2012/0201421 A1   Aug. 9, 2012

Related U.S. Application Data

(63) Continuation-in-part of application No. 12/910,445, filed on Oct. 22, 2010, now Pat. No. 8,503,745, which is a continuation-in-part of application No. 12/465,206, filed on May 13, 2009, now Pat. No. 8,238,631.

(51) Int. Cl.
   *G06K 9/00*   (2006.01)
(52) U.S. Cl.
   USPC .......................... 382/128; 382/131; 382/132
(58) Field of Classification Search
   CPC ................ G06T 7/0012; G06T 7/0083; G06T 2207/30004; G06T 2207/30081; A61B 19/5244; A61B 19/54
   USPC .................................. 382/128, 130, 131, 132
   See application file for complete search history.

(56) References Cited

U.S. PATENT DOCUMENTS

| | | | |
|---|---|---|---|
| 5,592,939 A | 1/1997 | Martinelli | |
| 5,913,820 A | 6/1999 | Bladen et al. | |
| 5,983,126 A | 11/1999 | Wittkampf | |
| 6,474,341 B1 | 11/2002 | Hunter et al. | |
| 6,609,022 B2 | 8/2003 | Vilsmeier et al. | |
| 6,940,941 B2 | 9/2005 | Gregerson et al. | |
| 7,001,045 B2 | 2/2006 | Gregerson et al. | |
| 7,106,825 B2 | 9/2006 | Gregerson et al. | |
| 7,108,421 B2 | 9/2006 | Gregerson et al. | |
| 7,188,998 B2 | 3/2007 | Gregerson et al. | |
| 7,570,791 B2 | 8/2009 | Frank et al. | |
| 7,751,865 B2 | 7/2010 | Jascob et al. | |

(Continued)

FOREIGN PATENT DOCUMENTS

EP   1561423 A1   8/2005

OTHER PUBLICATIONS

"AxiEM Electromagetic Navigation," tri-fold brochure, Medtronic Navigation (2005) 2 pages.

(Continued)

*Primary Examiner* — Gregory F Cunningham
(74) *Attorney, Agent, or Firm* — Harness, Dickey

(57) ABSTRACT

A patient defines a patient space in which an instrument can be tracked and navigated. An image space is defined by image data that can be registered to the patient space. A tracking device can be connected to a member in a known manner that includes imageable portions that generate image points in the image data. Selected image slices or portions can be used to register reconstructed image data to the patient space.

23 Claims, 19 Drawing Sheets

(56) References Cited

U.S. PATENT DOCUMENTS

| | | | |
|---|---|---|---|
| 7,899,226 B2 | 3/2011 | Pescatore et al. | |
| 8,238,631 B2 | 8/2012 | Hartmann et al. | |
| 8,503,745 B2 | 8/2013 | Simon et al. | |
| 2004/0019265 A1 | 1/2004 | Mazzocchi et al. | |
| 2004/0030236 A1 | 2/2004 | Mazzocchi et al. | |
| 2004/0030237 A1 | 2/2004 | Lee et al. | |
| 2004/0167391 A1 | 8/2004 | Solar et al. | |
| 2004/0167393 A1 | 8/2004 | Solar et al. | |
| 2004/0199072 A1 | 10/2004 | Sprouse et al. | |
| 2006/0029917 A1* | 2/2006 | Sui | 434/262 |
| 2007/0225599 A1 | 9/2007 | Solar et al. | |
| 2008/0216239 A1* | 9/2008 | Luginbuhl et al. | 5/601 |
| 2008/0242978 A1 | 10/2008 | Simon et al. | |
| 2009/0005668 A1 | 1/2009 | West et al. | |
| 2009/0022266 A1* | 1/2009 | Stayman et al. | 378/8 |
| 2009/0257551 A1 | 10/2009 | Dafni et al. | |
| 2010/0020926 A1 | 1/2010 | Boese et al. | |
| 2010/0063388 A1 | 3/2010 | Solar et al. | |
| 2010/0217120 A1 | 8/2010 | Solar et al. | |
| 2010/0290690 A1 | 11/2010 | Hartmann et al. | |
| 2011/0071389 A1 | 3/2011 | Simon et al. | |
| 2012/0201421 A1 | 8/2012 | Hartmann et al. | |
| 2012/0294491 A1 | 11/2012 | Hartmann et al. | |

OTHER PUBLICATIONS

"Solutions for Improved Surgeries, Navigation and Intra-Operative Imaging." Jul. 2007. Medtronic Navigation. pp. 1-21.

"Treon, StealthStation," brochure, Medtronic Surgical Navigation Technologies (2001) 8 pages.

International Search Report and Written Opinion mailed Jan. 18, 2012 for PCT/US2011/057204 claiming benefit of U.S. Appl. No. 12/910,445, filed Oct. 22, 2010.

Medtronic Navigation, "StealthStation® AXIEM™ Electromagnetic Navigation . . . ", 2005, www.stealthstation.com/physician/spine/library/axiem_ent.jsp, printed Aug. 19, 2006 (2 pages).

* cited by examiner

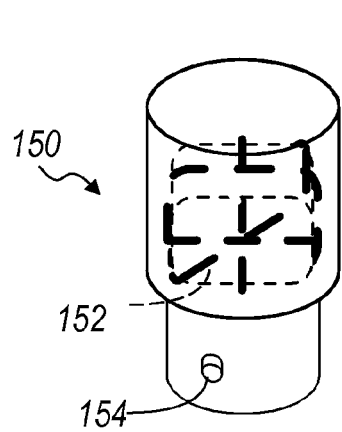
FIG. 4A
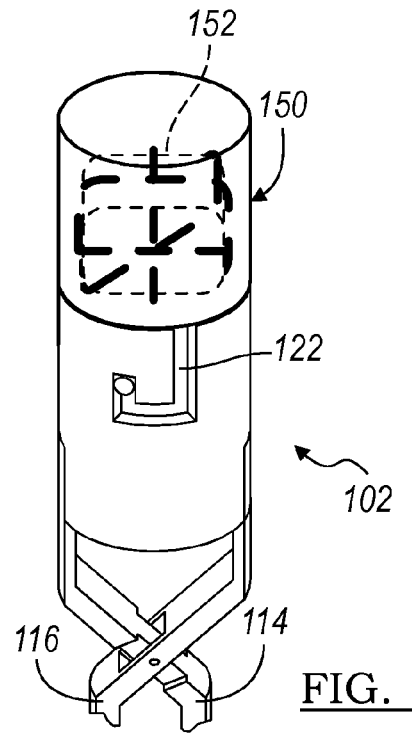
FIG. 4B
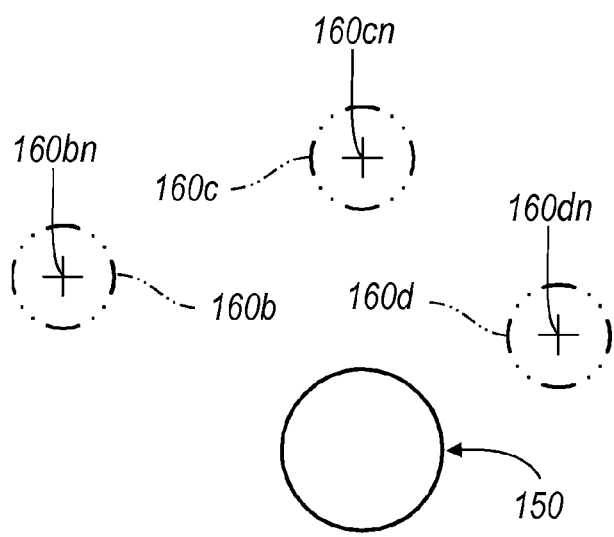
FIG. 4C
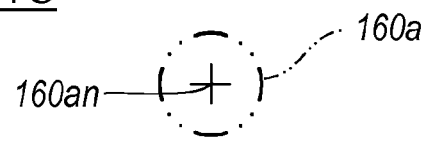

SYSTEM AND METHOD FOR AUTOMATIC REGISTRATION BETWEEN AN IMAGE AND A SUBJECT

CROSS-REFERENCE TO RELATED APPLICATIONS

This application is a continuation-in-part of Ser. No. 12/910,445, filed on Oct. 22, 2010, which is a continuation-in-part of U.S. patent application Ser. No. 12/465,206, filed on May 13, 2009. The entire disclosures of the above applications are incorporated herein by reference.

FIELD

The subject disclosure is related generally to an operative procedure and particularly to registration of image space to subject space.

BACKGROUND

This section provides background information related to the present disclosure which is not necessarily prior art.

An instrument can be navigated relative to a subject for performing various procedures. For example, a subject can include a patient on which a surgical procedure is being performed. During a surgical procedure, an instrument can be tracked in an object or subject space. In various embodiments the subject space can be a patient space defined by a patient. The location of the instrument that is tracked can be displayed on the display device relative to an image of the patient.

The position of the patient can be determined with a tracking system. Generally, a patient is registered to the image, via tracking an instrument relative to the patient to generate a translation map between the subject or object space (e.g. patient space) and the image space. This often requires time during a surgical procedure for a user, such as a surgeon, to identify one or more points in the subject space and correlating, often identical points, in the image space.

Only after registration can the position of the instrument be appropriately displayed on the display device. The position of the instrument relative to the subject can be displayed as an icon on the display device.

SUMMARY

This section provides a general summary of the disclosure, and is not a comprehensive disclosure of its full scope or all of its features.

According to various embodiments, a fiducial object can be imaged. The fiducial object can include an array of discrete spheres, discrete objects of various shapes, a continuous and/or one or more curved rods that can all be in one or intersect one plane. The fiducial object can be modeled in three-dimensional (3D) space as a 3D model. Fiducial features can be extracted from the 3D model. The fiducial features can be compared to or coordinated with image fiducial features that are the imaged fiducial object or some portion thereof (e.g. an image fiducial feature can be a point relating to a center of a sphere or a circle or point relating to an intersection of a rod with a plane).

According to various embodiments, a method to register a subject space defined by a subject to an image space is disclosed. The method includes attaching an imageable fiducial assembly to the subject and acquiring a plurality of two-dimensional x-ray projection image data of the subject with an imaging device at selected parameters for each of the plurality of two-dimensional x-ray projection image data. A three dimensional reconstruction is generated based on the acquired plurality of two-dimensional x-ray projection image data and at least one of the plurality of acquired two-dimensional x-ray projection image data is selected that includes a selected portion of the imageable fiducial assembly. From a storage device selected parameters of the imaging device are recalled that relate to the selected at least one of the plurality of acquired two-dimensional x-ray projection image data and a synthetic digital radiograph reconstruction is generated of the imageable fiducial assembly at parameters similar to the recalled parameters of the imaging device. A registration of the selected at least one of the plurality of acquired two-dimensional x-ray projection image data to the generated synthetic digital radiograph reconstruction of the imageable fiducial assembly can then occur.

According to various embodiments, a method to register a subject space defined by a subject to an image space is disclosed. The method includes selecting a region of the subject about which to acquire image data and affixing a fiducial assembly relative to the selected region, wherein the fiducial assembly includes a base and an imageable fiducial portion. The method can then further include acquiring a plurality of two-dimensional x-ray projections of the selected region with an imaging device and storing the plurality of two-dimensional x-ray projections along with imaging device parameters for each of the plurality of two-dimensional x-ray projections. A sub-plurality of the plurality of two-dimensional x-ray projections can be selected that include a selected amount of image data information regarding the imageable fiducial portion. Imaging device parameters for the selected sub-plurality of the plurality of two-dimensional x-ray projections can be recalled and synthetic digital radiograph reconstruction based on a three-dimensional model of at least the imageable fiducial portion can be generated based on the recalled imaging device parameters. A registration of the generated synthetic digital radiograph reconstructions to the selected sub-plurality of the plurality of two-dimensional x-ray projections can occur.

According to various embodiments, a system to allow registration of a subject space to an image space in an image data is disclosed. The system can include a fiducial assembly having a plurality of fiducial imageable portions fixedly positioned relative to a base member that is operable to be fixed to a subject defining the subject space and an imaging system configured to acquire x-ray projections of the subject and the fiducial imageable portions at known imaging system parameters. The system can further include a first processing system operable to generate a three dimensional reconstruction of the x-ray projections to define the image space, wherein the three dimensional reconstruction fails to include three dimensional reconstruction of the fiducial imageable portions. A second processing system can generate synthetic digital radiograph reconstructions of the fiducial imageable portions based on the known imaging system parameters of images acquired of the fiducial imageable portions. Also, a third processing system can register selected x-ray projections including images of at least a portion of the plurality of fiducial imageable portions with the generated synthetic digital radiograph reconstructions of the fiducial imageable portions.

The tracking of an instrument during a procedure, such as a surgical or operative procedure, allows for navigation of a procedure. When image data is used to define an image space it can be correlated or registered to a physical space defined by a subject, such as a patient. According to various embodiments, therefore, the patient defines a patient space in which an instrument can be tracked and navigated. The image space defined by the image data can be registered to the patient space defined by the patient. The registration can occur with the use of fiducials that can be identified in the image data and in the patient space.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 3A-4C are plan views of an imageable and trackable device, according to various embodiments;

Corresponding reference numerals indicate corresponding parts throughout the several views of the drawings.

DETAILED DESCRIPTION

Example embodiments will now be described more fully with reference to the accompanying drawings.

Figure 1:
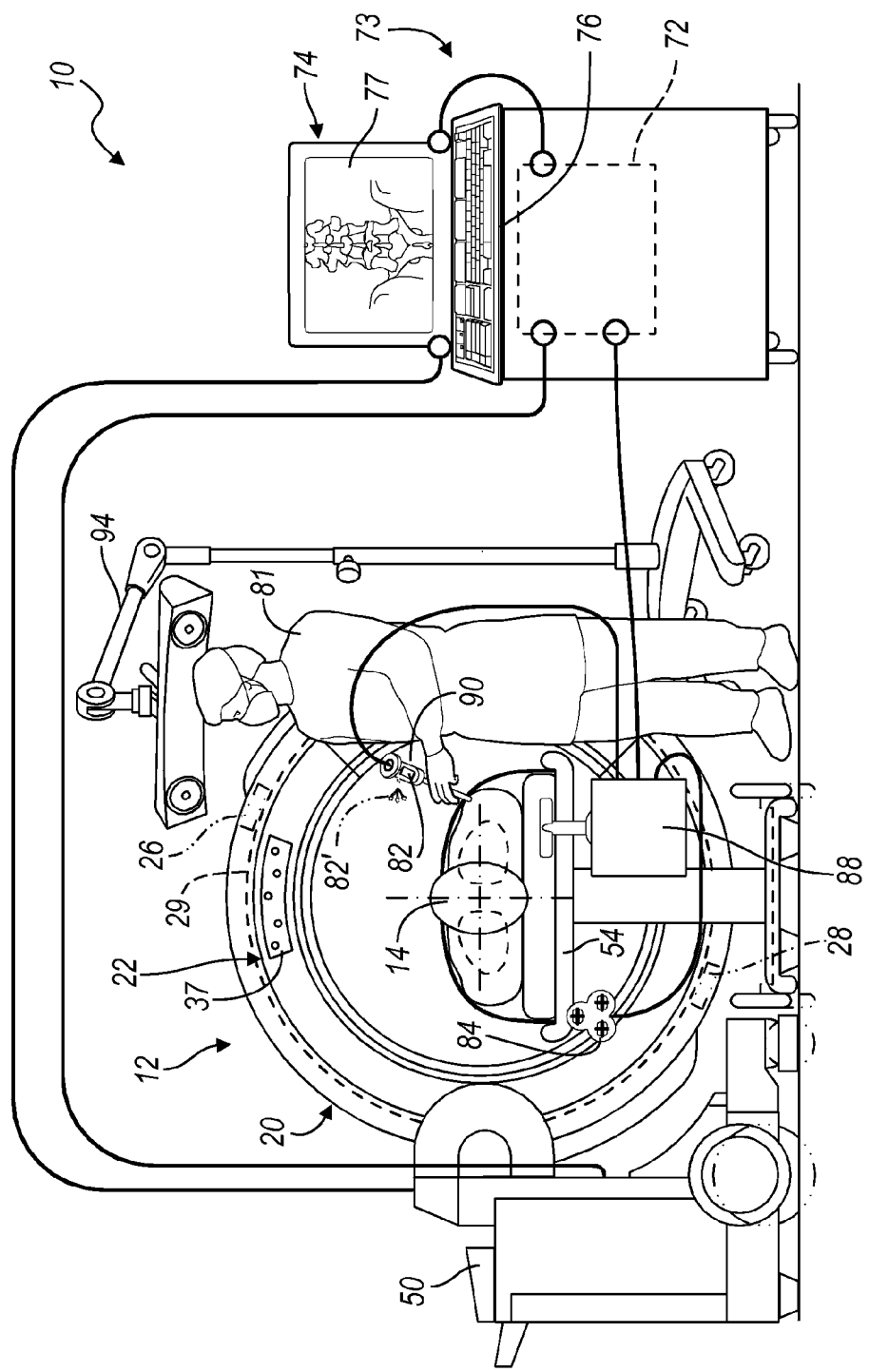
FIG. 1 is diagrammatic view illustrating an overview of a navigation system, according to various embodiments.
Figure 2:
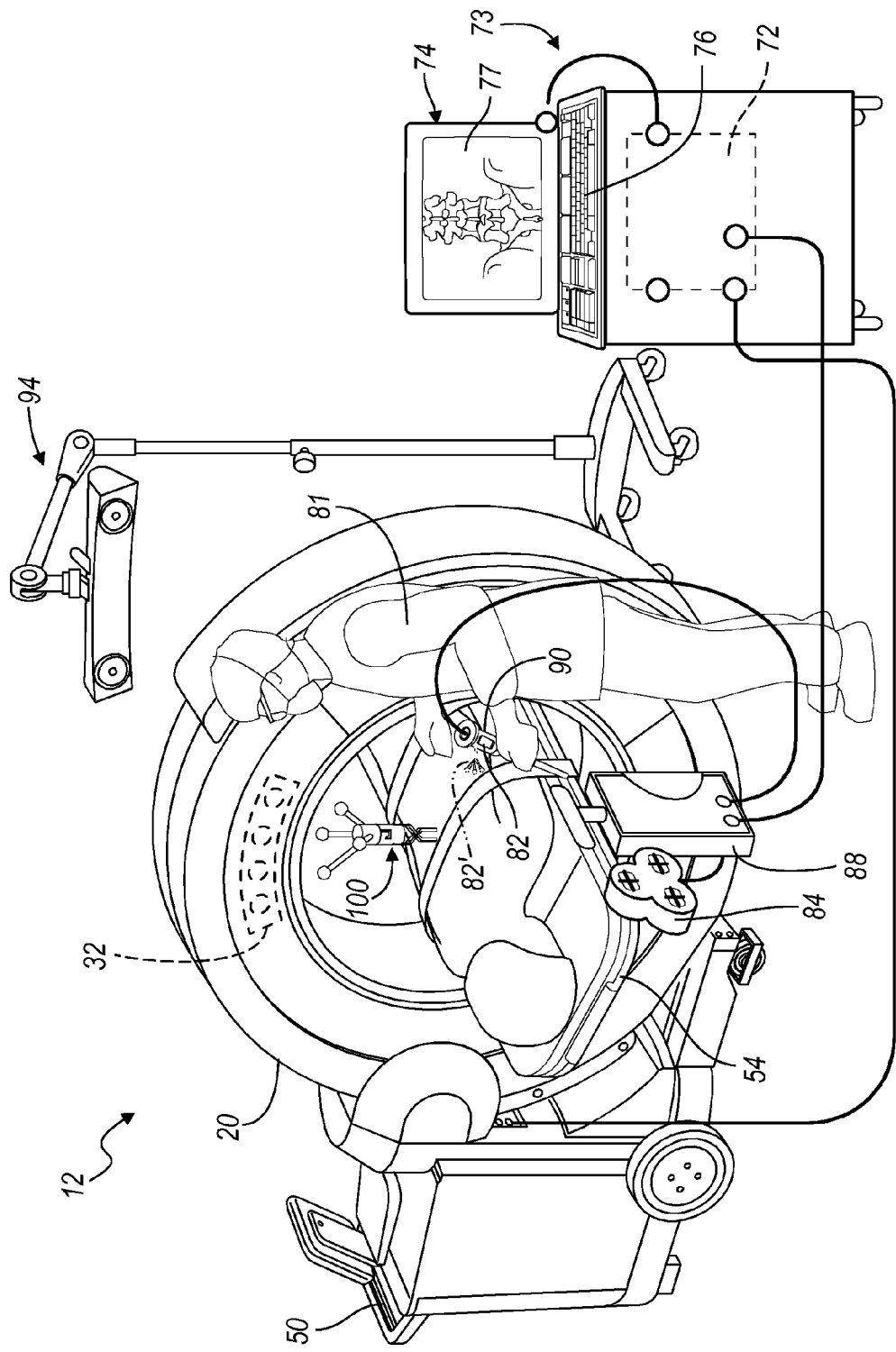
FIG. 2 is diagrammatic alternative view of the system of FIG. 1, according to various embodiments.

FIGS. 1 and 2 are diagrammatic views illustrating an overview of a navigation system 10 that can be used for various procedures. The navigation system 10 can be used to track the location of an implant, such as a spinal implant or orthopedic implant, relative to a patient 14. Also, the navigation system 10 can track the position and orientation of an instrument 90, such as a biopsy needle or resection instrument. It should further be noted that the navigation system 10 may be used to navigate any type of instrument, implant, or delivery system, including: guide wires, arthroscopic systems, orthopedic implants, spinal implants, deep brain stimulation (DBS) probes, etc. Moreover, the instruments may be used to navigate or map any region of the body. The navigation system 10 and the various instruments may be used in any appropriate procedure, such as one that is generally minimally invasive or an open procedure.

The navigation system 10 includes an imaging device 12 that is used to acquire pre-, intra-, or post-operative or real-time image data of a subject, such as a patient 14. It will be understood, however, that any appropriate subject can be imaged and any appropriate procedure may be performed relative to the subject. In the example shown, the imaging device 12 comprises an O-arm® imaging device sold by Medtronic Navigation, Inc. having a place of business in Louisville, Colo., USA. The imaging device 12 may have a generally annular gantry housing 20 and an image capturing portion 22. The image capturing portion 22 may include an x-ray source or emission portion 26 and an x-ray receiving or image receiving portion 28 located generally or as practically possible 180 degrees from each other and mounted on a rotor (not illustrated) relative to a track or rail 29. The image capturing portion 22 can be operable to rotate 360 degrees during image acquisition. The image capturing portion 22 may rotate around a central point or axis, allowing image data of the patient 14 to be acquired from multiple directions or in multiple planes. The imaging device 12 can include those disclosed in U.S. Pat. Nos. 7,188,998; 7,108,421; 7,106,825; 7,001,045; and 6,940,941; all of which are incorporated herein by reference, or any appropriate portions thereof. In one example, the imaging device 12 can utilize flat plate technology having a 1,720 by 1,024 pixel viewing area.

The position of the image capturing portion 22 can be precisely known relative to any other portion of the imaging device 12. The imaging device 12, according to various embodiments, can know and recall precise coordinates relative to a fixed or selected coordinate system. This can allow the imaging system 12 to know its position relative to the patient 14 or other references. In addition, as discussed herein, the precise knowledge of the position of the image capturing portion 22 can be used in conjunction with a tracking system to determine the position of the image capturing portion 22 and the image data relative to the tracked subject, such as the patient 14.

The imaging device 12 can also be tracked with a tracking device 37. The image data defining an image space acquired of the patient 14 can, according to various embodiments, be inherently or automatically registered relative to an object space. The object space can be the space defined by a patient 14 in the navigation system 10. The automatic registration can be achieved by including the tracking device 37 on the imaging device 12 and/or the determinable precise location of the image capturing portion 22. According to various embodiments, as discussed herein, imageable portions, virtual fiducial points and other features can also be used to allow for registration, automatic or otherwise. It will be understood, however, that image data can be acquired of any subject which will define subject space. Patient space is an exemplary subject space. Registration allows for a translation between patient space and image space.

The patient 14 can also be tracked or fixed within the navigation system 10 to allow for registration. As discussed further herein, registration of the image space to the patient space or subject space allows for navigation of the instrument 90 with the image data. When navigating the instrument 90, a position of the instrument 90 can be illustrated relative to image data acquired of the patient 14 on a display device 74. Various tracking systems, such as one including an electromagnetic (EM) localizer 84 or an optical localizer 94 can be used to track the instrument 90.

More than one tracking system can be used to track the instrument 90 in the navigation system 10. According to various embodiments, these can include an electromagnetic tracking (EM) system having an EM localizer 84 and an optical tracking system having an optical localizer 94. Either or both of the tracking systems can be used to tracked selected tracking devices, as discussed herein. It will be understood, unless discussed otherwise, that a tracking device can be a portion trackable with a selected tracking system. A tracking device need not refer to the entire member or structure to which the tracking device is affixed or associated.

It is appreciated, however, that an imaging device other than the imaging device 12, such as a fluoroscopic C-arm can be used. Other exemplary fluoroscopes include bi-plane fluoroscopic systems, ceiling mounted fluoroscopic systems, cath-lab fluoroscopic systems, fixed C-arm fluoroscopic systems, isocentric C-arm fluoroscopic systems, 3D fluoroscopic systems, etc. Other appropriate imaging systems can also include MRI, CT, ultrasound, etc.

An imaging device controller 50 that may control the imaging device 12 can receive the image data generated at the image capturing portion 22 and store the images for later use. The controller 50 can also control the rotation of the image capturing portion 22 of the imaging device 12. It will be understood that the controller 50 need not be integral with the processing unit or processing portion 36 and may include a second and separate processor, such as that in a portable computer.

The patient 14 can be fixed onto an operating table 54. According to one example, the table 54 can be an Axis Jackson® operating table sold by OSI, a subsidiary of Mizuho lkakogyo Co., Ltd., having a place of business in Tokyo, Japan or Mizuho Orthopedic Systems, Inc having a place of business in California, USA. Patient positioning devices can be used with the table, and include a Mayfield® clamp or those set forth in commonly assigned U.S. patent application Ser. No. 10/405,068 entitled "An Integrated Electromagnetic Navigation And Patient Positioning Device", filed Apr. 1, 2003 which is hereby incorporated by reference.

The position of the patient 14 relative to the imaging device can be determined by the navigation system 10. The tracking device 37 can be used to track and locate at least a portion of the imaging device 12, for example the housing 20. The patient 14 can be tracked with a tracking device, such as one used as a dynamic reference frame, as discussed further herein. Accordingly, the position of the patient 14 relative to the imaging device 12 can be determined. Further, the location of the imaging portion 22 can be determined relative to the housing 20 due to its precise position on the rail 29 within the housing 20, substantially inflexible rotor, etc. The imaging device 12 can include an accuracy of within 10 microns, for example, if the imaging device 12 is an O-Arm® imaging device sold by Medtronic Navigation, Inc. having a place of business in Louisville, Colo. Precise positioning of the imaging portion 22 is further described in U.S. Pat. Nos. 7,188, 998; 7,108,421; 7,106,825; 7,001,045; and 6,940,941; all of which are incorporated herein by reference, In operation, the imaging device 12 can generate and/or emit x-rays from the x-ray source 26 that propagate through the patient 14 and are received by the x-ray imaging receiving portion 28. The image capturing portion 22 generates image data representing the intensities of the received x-rays. Typically, the image capturing portion 22 can include an image intensifier that first converts the x-rays to visible light and a camera (e.g. a charge couple device) that converts the visible light into digital image data. The image capturing portion 22 may also be a digital device that converts x-rays directly to digital image data for forming images, thus potentially avoiding distortion introduced by first converting to visible light.

Two dimensional and/or three dimensional fluoroscopic image data that may be taken by the imaging device 12 can be captured and stored in the imaging device controller 50. Multiple image data taken by the imaging device 12 may also be captured and assembled to provide a larger view or image of a whole region of a patient 14, as opposed to being directed to only a portion of a region of the patient 14. For example, multiple image data of the patient's 14 spine may be appended together to provide a full view or complete set of image data of the spine.

The image data can then be forwarded from the image device controller 50 to a navigation computer and/or processor system 72 that can be a part of a controller or work station 73 having the display 74 and a user interface 76. It will also be understood that the image data is not necessarily first retained in the controller 50, but may also be directly transmitted to the work station 73. The work station 73 can provide facilities for displaying the image data as an image 77 on the display 74, saving, digitally manipulating, or printing a hard copy image of the received image data. The user interface 76, which may be a keyboard, mouse, touch pen, touch screen or other suitable device, allows a user 81 to provide inputs to control the imaging device 12, via the image device controller 50, or adjust the display settings of the display 74. The work station 73 may also direct the image device controller 50 to adjust the image capturing portion 22 of the imaging device 12 to obtain various two-dimensional images along different planes in order to generate representative two-dimensional and three-dimensional image data.

With continuing reference to FIG. 1, the navigation system 10 can further include a tracking system such as an electromagnetic (EM) navigation tracking system. The EM tracking system can include a localizer, such as a transmitter coil array 84. The EM tracking system can also include an EM controller and interface portion 88 and a tracking device 82 associated with the instrument 90. The EM controller 88 can be connected to the processor portion 72, which can include a processor included within a computer. The localizer or transmitter coil array 84 can be attached directly to the image device 12, attached to the OR table 54, or any other appropriate location. The EM tracking system may include the STEALTHSTATION® AXIEM™ Navigation System, sold by Medtronic Navigation, Inc. having a place of business in Louisville, Colo.; or can be the EM tracking system described in U.S. patent application Ser. No. 10/941,782, filed Sep. 15, 2004, and entitled "METHOD AND APPARATUS FOR SURGICAL NAVIGATION"; U.S. Pat. No. 5,913,820, entitled "Position Location System," issued Jun. 22, 1999; and U.S. Pat. No. 5,592,939, entitled "Method and System for Navigating a Catheter Probe," issued Jan. 14, 1997; all of which are herein incorporated by reference. It will be understood that the tracking system 82 may also be or include any appropriate tracking system, including a STEALTHSTATION® TREON® or S7™ tracking systems having an optical localizer, similar to the optical localizer 94, and sold by Medtronic Navigation, Inc. of Louisville, Colo. Other tracking systems include an acoustic, radiation, radar, etc. The tracking systems can be used according to generally known or described techniques in the above incorporated references. Details will not be included herein except when to clarify selected operation of the subject disclosure.

Wired or physical connections can interconnect the tracking systems, imaging device 12, etc. Alternatively, various portions, such as the instrument 90, may employ a wireless communications channel, such as that disclosed in U.S. Pat. No. 6,474,341, entitled "Surgical Communication Power System," issued Nov. 5, 2002, herein incorporated by reference, as opposed to being coupled directly to the EM controller 88. Also, the tracking device 82 can generate a field sensed by the coil array 84 to track the tracking device 82.

Various portions of the navigation system 10, such as the instrument 90, and others as will be described in detail below, can be equipped with at least one, and generally multiple, of the tracking devices 82. The instrument can also include more than one type or modality of tracking device, such as the EM tracking device 82 and an optical tracking device 82'. The instrument 90 can include a graspable or manipulable portion at a proximal end and the tracking devices 82, 82' may be fixed near the manipulable portion of the instrument 90.

Additional representative or alternative localization and tracking system is set forth in U.S. Pat. No. 5,983,126, entitled "Catheter Location System and Method," issued Nov. 9, 1999, which is hereby incorporated by reference. The navigation 10 system may be a hybrid system that includes components from various tracking systems.

According to various embodiments, the navigation system 10 can be used to track the instrument 90 relative to the patient 14. The instrument 90 can be tracked with the tracking system, as discussed above. Image data of the patient 14, or an appropriate subject, can be used to assist the user 81 in guiding the instrument 90. The image data, however, is registered to the patient 14. The image data defines an image space that is registered to the patient space defined by the patient 14. The registration can be performed as discussed herein, automatically, manually, or combinations thereof.

Generally, registration allows a translation map to be generated of the physical location of the instrument 90 relative to the image space of the image data. The translation map allows the tracked position of the instrument 90 to be displayed on the display device 74 relative to the image data 77. An icon 90$i$ (FIGS. 5 and 8) can be used to illustrate the location of the instrument relative to the image data 77.

Figure 3A:
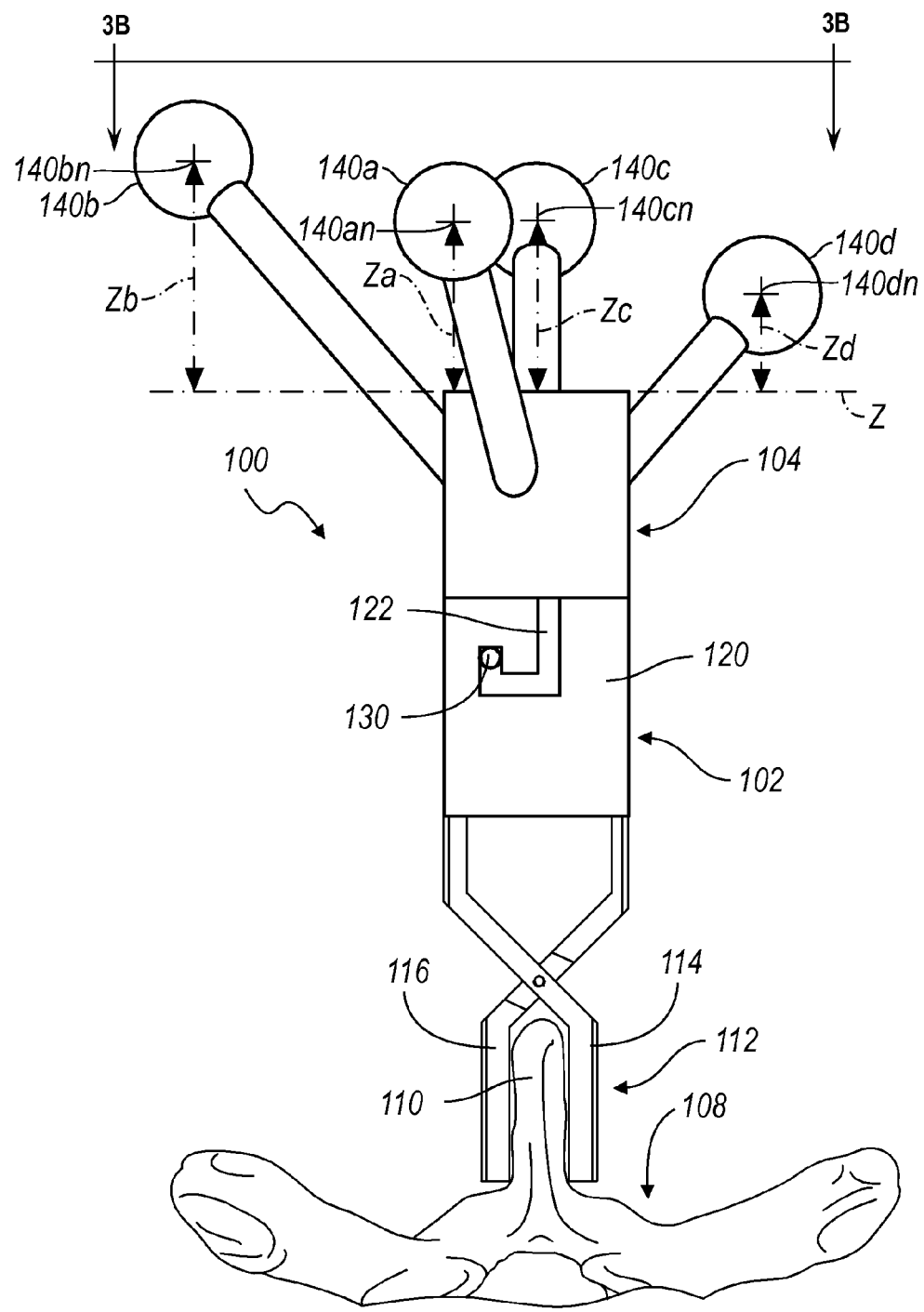
Figure 3B:
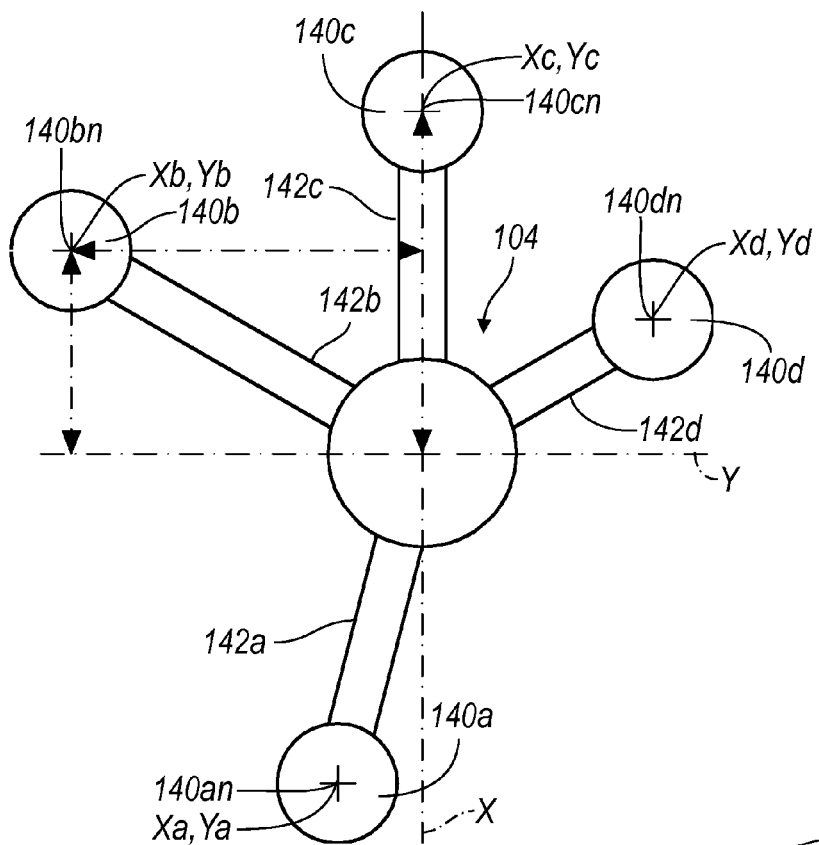

A registration system or method can use a fiducial assembly 100, is illustrated in FIGS. 3A and 3B. The fiducial assembly 100 can include a clamp or other fixation portion 102 and an imageable fiducial body 104. The fixation portion 102 can be provided to fix any appropriate portion, such as a portion of the anatomy. As illustrated in FIGS. 1 and 2, the fiducial assembly 100 can be interconnected with a portion of a spine 108 such as a spinous process 110.

The fixation portion 102 can be interconnected with a spinous process 110 in any appropriate manner. For example, a pin or a screw can be driven into the spinous process 110. Alternatively, or in addition thereto, a clamp portion 112 can be provided to interconnect the spinous process 110. A first clamp leg 114 and a second clamp leg 116 can be driven or moved together to bind or fixedly connect with the spinous process 110. The movement of the clamping legs 114, 116 can be in any appropriate manner.

The fixation member 112 can further include a seat or seat body 120. The seat body 120 can include a key groove or locking portion 122, which can be defined as a J-groove 122. The J-groove 122 can terminate at an opening at the top of the seat portion 120, as illustrated in FIG. 3C. A locking portion or extension, as discussed herein, can cooperate with the J-groove 122 to hold a member relative to the seat 120. Any portion being held relative to the seat 120 can include a resilient member to move the locking portion into the tip or locking region 122$a$ of the J-groove 122. When a locking portion is within the locking region 122$a$, the member positioned relative to the seat 120 is positioned at a known and fixed location relative to the seat 120. This can be used for repeatedly placing a member relative to the base 102 or a subject, such as the patient 14.

Figure 3D:
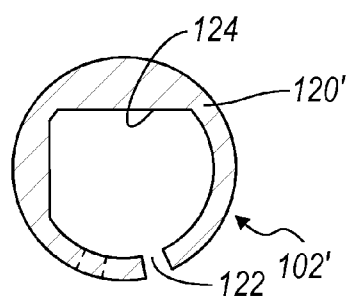
Figure 3C:
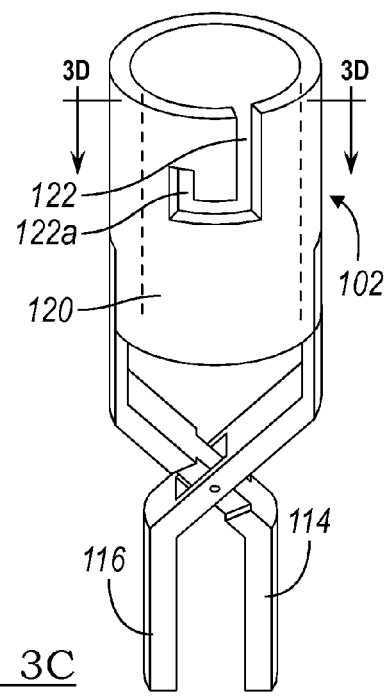

With reference to FIG. 3D, an alternative seat body 120' is illustrated. The alternative seat body 120' can be a portion of an alternative base portion or fixation member 102. The alternative seat body 120' can include a flat or keyed portion 124. A member positioned relative to the alternative seat portion 120' can be positioned relative to the seat portion 120 in a known configuration due to the keyed configuration which allows only a limited number of rotational positions of the member. It will be understood that a locking groove, such as the locking groove 122, can also be provided in conjunction with the keyed walls 124.

The fixation member 102, 102' can be fixed to a subject, such as the patient 14. With the keyed or fixation grooves or portions, a member positioned relative to the fixation base 102 can be positioned in a known and fixed position. The keyed walls 124 or the J-groove 122 can rotationally and axially hold a member relative to the fixation base 102. As discussed further herein, this can fix a member in three dimensional space relative to the subject to which the base 102 is fixed and assists in defining at least six degrees of freedom relative to the subject.

The imageable body 104 can be interconnected with the seat body 120 by including a connection portion that can define a key interaction portion or rod 130. It will be further understood that the imageable portion 104 can also include a configuration to cooperate or interact with the polygonal sides 124 of the seat body 120', as illustrated in FIG. 3D. As discussed further herein, the interconnection, either or both with the key slot 122 or the polygonal portion 124, allows for the imageable body 104 to be positioned relative to the fixation member 102 in a substantially repeatable and in a known configuration.

The imageable body 104 can include one or more imageable sections or portions, such as a first imageable portion 140$a$, a second imageable portion 140$b$, a third imageable portion 140$c$, and a fourth imageable portion 140$d$. It will be understood that the imageable portions 140$a$-140$d$ can include regions defined substantially only by a spherical portion at an end of extensions 142$a$-142$d$, the entire imageable body 104 can be imageable, or any selected portion thereof. For example, if only the spheres of the imageable portions 140$a$-140$d$ are imageable, the image acquired of the imageable body 104 can include only images of four points defined by the imageable portions 140$a$-140$d$. It will be understood, however, that any appropriate imageable configuration can be defined by the imageable body 104, such as providing portions of the extension arms 142$a$-142$d$ that are also imageable. The discussion herein to the imageable portions 140$a$-140$d$ is for simplicity of the current discussion.

As discussed above, the imageable body 104 can be positioned or fixed relative to the fixation body 102 and in a known and selected manner. Accordingly, each of the imageable portions 140$a$-140$d$ can be positioned at a fixed and different location in three dimensional space. Each of the imageable portions 140$a$-140$d$ can include a center 140$an$-140$dn$. Each of the centers 140$an$-140$dn$ can be positioned at a selected and different heights Za-Zd relative to a Z axis Z. The centers 140$an$-140$dn$ can be further positioned relative to X and Y axes at known locations Xa, Ya-Xd, Yd. Accordingly, each of the imageable portions 140$a$-140$d$ can include a center positioned at known and different three dimensional locations Xa, Ya, Za-Xd, Yd, Zd. When each of the centers 140an-140dn include a different three dimensional location, the information in the image data, as discussed further herein, also includes different three dimensional locations and allows for identification of multiple points in three dimensional space for registration.

When the imageable portions 140a-140d are imaged with the imaging device 12, image data is generated that includes or identifies the imageable portions 140a-140d. As discussed further herein, the imageable portions 140a-140d can be identified in image data automatically, such as with a processor executing a program, manually, or combinations thereof. Methods of automatic imageable portion identification include those disclosed in U.S. Patent Application Publication No. 2008/0242978, (U.S. patent application Ser. No. 11/693,558) filed on Mar. 29, 2007, incorporated herein by reference. Manual identification can include selecting a cantor or region in the image data wherein the imageable portion has been imaged. Regardless, the imageable portions 140a-140d identified in the image data can be used as fiducial points or positions that can be used to register the image data or the image space of the image data with patient space.

With reference to FIGS. 4A and 4B, a tracking device 150 is illustrated. The tracking device 150 can be tracked with any appropriate tracking system, such as an EM tracking system. The tracking device 150 can include an electromagnetic coil or coil array portion 152. It will be understood, however, that the tracking device 150 can include any appropriate tracking device. For example, the tracking device 150 can include an optical tracking portion, an acoustic tracking portion, or any other appropriate tracking portion. Further, the tracking device 150 can transmit, receive, or combinations thereof a signal or radiation for tracking the tracking device 150.

The tracking device 150 can further include a peg or rod 154 that is operable to interconnect with the groove portion 122 of the base 102, as specifically illustrated in FIG. 4B. The tracking device 150 can further include portions that cooperate with the keyed flats 124 of the alternative base 102', illustrated in FIG. 3D. Accordingly, the tracking device 150 can be connected with the fixation base 102 in a manner that is in a substantially similar or identical and/or known orientation and position relative to the base 102 as the imageable body 104. In this manner, the tracking device 150 can be connected with the mounting base 102 in a known configuration and orientation. The tracking device 150 can therefore be tracked relative to any portion, such as the spinal process 110 to which the base 102 is connected.

The tracking device 150 can be calibrated relative to the mounting base 102 to provide information or orientation coordinates. For example, the tracking device 150 can be calibrated to identify or located four virtual points 160a-160d. Each of the virtual points 160a-160d can include or define a center 160an-160dn. Each of the virtual points 160a-160d or the centers thereof 160an-160dn can include three dimensional coordinates that substantially correspond or are identical to the X, Y and Z coordinates Xa, Ya, Za-Xd, Yd, Zd. Accordingly, the virtual points 160a-160d can substantially overlay or be positioned in space at the same physical locations as the imageable portions 140a-140d. Because the tracking device 150 can be interconnected with the fixation base 102 in a known manner, the tracking device and the virtual points 160a-160d are at known or identical positions as the imageable body 104 relative to the base 102. The virtual points 160a-160d can correspond to the physical locations of the imageable portions 140a-140d of the imageable body 104 and also be referred to as virtual fiducial points 160a-160d.

The virtual points 160a-160d can be aligned with the physical location of the imageable portions 140a-140d due to the keyed connection.

It will be understood, however, that the virtual points 160a-160d can simply be positioned with a known location relative to the physical location of the imageable portions 140a-140d when the tracking device 150 is interconnected with the base 102. The virtual points can be positioned at substantially the same location or any known location relative to the imageable portions 140a-140d. Further, because the virtual points 160a-160d each include a three dimensional location that is similar and/or known relative to the three dimensional location of the imageable portions 140a-140d, and because the tracking device 150 is fixed relative to the subject, position information with six degrees of freedom can be determined by tracking the tracking device 150.

Figure 5:
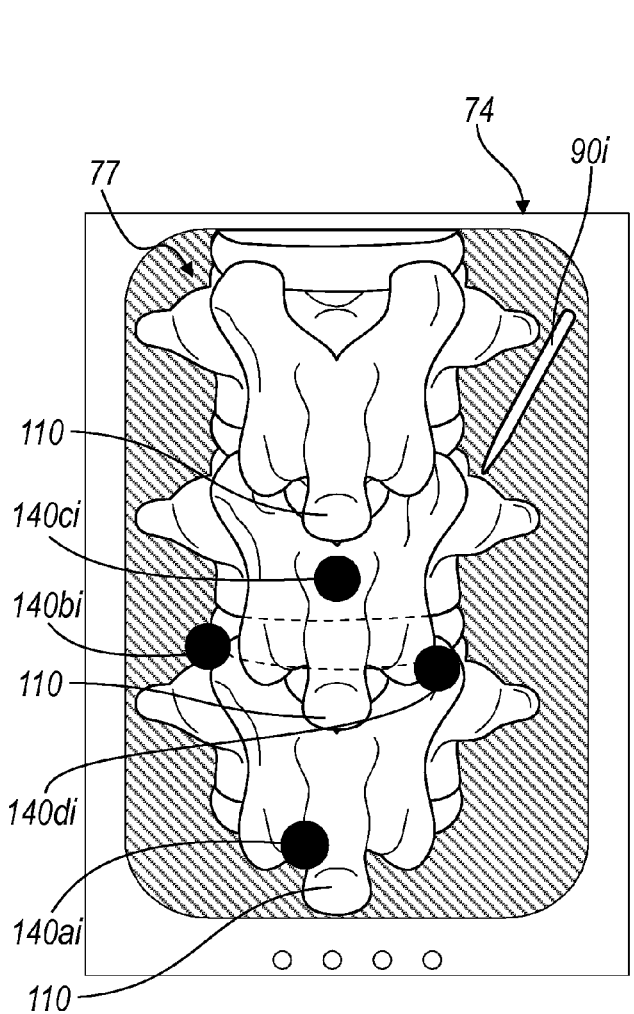
FIG. 5 is a diagram of image data.

With reference to FIG. 5, image data generated with an appropriate imaging device, can generate image data of the imageable body 104 to identify the imageable portions 140a-140d. The display 74 can include or display the image data 77 that includes images of the anatomy, such as the spinal process 110, and the imageable portions 140a-140d illustrated as points or dots 140ai-140di. The location of the points 140ai-140di in the image data can be used for registration, as discussed herein.

Figure 6:
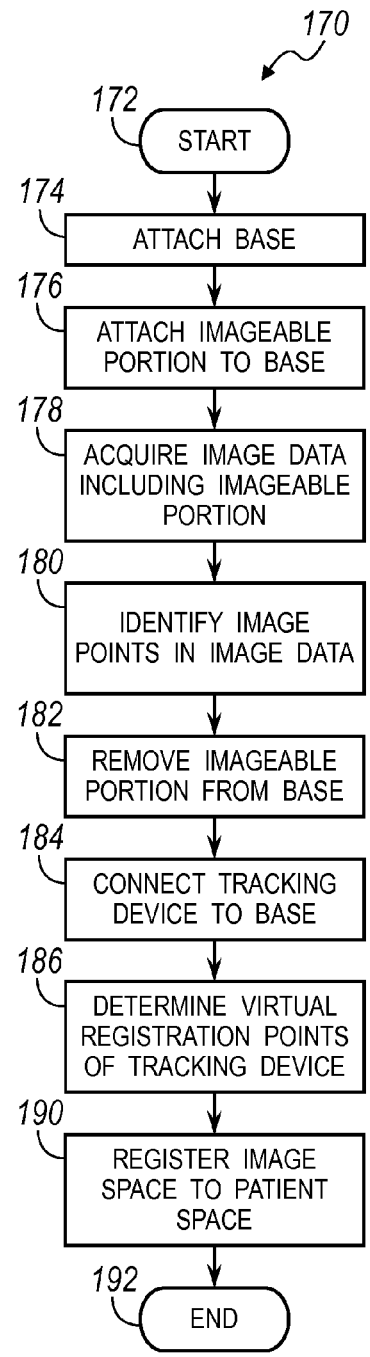
FIG. 6 is a flowchart of a method for registering image space to patient space.

With reference to FIG. 6, a method 170 is illustrated in a flow chart to acquire image data of the patient 14 and register the patient 14 to the image data 77, substantially automatically. With reference to FIG. 6, and continuing reference to FIGS. 1-5, the method can start in start block 172. The base 102 can be attached in block 174. The imageable body 104 can then be attached to the base in block 176. It will be understood, however, that the imageable body 104 can be incorporated with the base 102 prior to attachment of the base 102 or can be connected at any appropriate time. Further, the base 102 can be attached to any appropriate subject or portion of the subject, such as a spinal process 110.

Once the imageable body 104 and the base 102 are interconnected with the subject, image data can be acquired including the imageable body 104 in block 178. As discussed above, the image data can include any appropriate image data, such as an x-ray or CT or MRI, or any appropriate image data. Accordingly, the imageable portions 140a-140d of the imageable body 104 can be imageable with any appropriate or multiple imaging modalities. For example, the image data can be acquired using the O-Arm®, sold by Medtronic Navigation, Inc. having a place of business in Colo., USA. The imaging device can further include the imaging device disclosed in U.S. Pat. Nos. 7,188,998; 7,108,421; 7,106,825; 7,001,045; and 6,940,941, all incorporated herein by reference.

Once the image data has been acquired in block 178, the image points 140ai-140di, such as the points generated in the image data and by the imageable portions 140a-140d, can be identified in block 180. As illustrated in FIG. 5, the image points 140ai-140di can be generated in the image data 77. Accordingly, a program or system can be used to identify and locate the image points 140ai-140di. It will be understood that the image points 140ai-140di can be identified in any appropriate coordinate system. For example, it will be understood that the image points 140ai-140di can be identified in two, three, or four dimensions depending upon the image data acquired in block 178.

In identifying the imageable points 140ai-140di, the navigation system 10 or the user 81 can also identify the three dimensional coordinates in the image data that corresponds to the three dimensional coordinates of the imageable portions 140a-140d. Accordingly, the location of the image points 140ai-140di can be identified and located in the image data 77 in three dimensions. As discussed above, the location of the imageable points 140ai-140di can identify three dimensional points in the image data 77. Further, because the imageable body 104 is fixed to the base 102, which is further fixed to the subject, the image points 140ai-140di can be used to identify three dimensional locations, or a plurality of locations, in the image data relative to the subject.

The imageable body 104 can be removed from the base in block 182. The tracking device 150 can then be connected to the base in block 184. As discussed above, and illustrated in FIGS. 4A-4C, the tracking device 150 can be connected to the base 102 that is maintained in connection with the spinal process 110. Due to the connection, such as the keyed connection of the tracking device 150 with the base 102, the tracking device 150 can be positioned with a known location and orientation relative to the base 102. The fixation can be both axially and rotationally to assure a six degree of freedom tracking of the tracking device 150. Accordingly, connecting the tracking device 150 to the base 102 in block 184 can orient the tracking device 150 relative to the base 102 according to a known configuration and orientation. The known configuration can be known by the navigation system, such as by calling it from memory or entering data by the user 81. As further discussed above, the positioning of the tracking device 150 relative to the base 102 can allow the tracking device 150 to determine or transmit virtual coordinates in the navigation system 10.

Virtual fiducial points can be determined in block 186 and can be determined by identifying or tracking the location of the virtual points 160a-160d with the tracking device 150. The virtual points 160a-160d, also referred to as virtual registration points, can be located in the navigation system 10, according to any known tracking modality. The virtual registration points 160a-160d can be identified in the subject space including the three dimensional coordinates of each of the virtual points. The identification of the virtual points can include identifying the tracking device 150 in the navigation system 10 to determine or input the calibrated or known location of the virtual points. As discussed above, the tracking device 150 can include the electromagnetic tracking sensor 152 that can be tracked with the electromagnetic localizer 84.

After identifying the image points 140ai-140di in the image data in block 180 and determining the virtual registration points 160a-160d of the tracking device in block 186, a registration of the image space to patient space can be made in block 190. Registration of the image space to the patient space can be performed because the identified image points 140ai-140di are in image space and the virtual fiducial points 160a-160d are defined by the tracking device 150 connected to the patient 14 in patient space. Accordingly, once the location of the image points 140ai-140di are identified in the image data in block 180, and the locations of the virtual fiducial points 160a-160d are identified in patient space in block 186, the registration can occur between the image space and the patient space. As discussed above, the locations of the virtual fiducial points 160a-160d in the subject space can be substantially identical to or at known locations relative to the physical locations of the imageable portions 140a-140d. Accordingly, the identical or known locations allow for registration as discussed further herein.

During registration, a translation map is determined between the image data coordinate system of the image data acquired in block 178 and the patient space defined by the patient 14. Once the registration occurs, the instrument 90 can be tracked with the tracking system that is registered to the image data to allow an identification and illustration of a position of the tracked instrument 90 as an icon superimposed on the image data. The registration procedure can then end in block 192.

Once the image data is registered to the patient space in block 190, tracking of the tracking device can occur according to any appropriate method or system, including those discussed above. Further, the method 170 can be carried out substantially automatically with a processor, such as the processor 72 of the workstation 73. The method 170 can be substantially automatic due to the identification of the image points 140ai-140di in the image data 180 and the determination of the virtual registration points 160a-160d of the tracking device 150 in block 186. Both of these determinations or identifications can be done substantially with a processor that is programmed or inputted with the calibrated data of the imageable portions 140a-140d and the virtual registration points 160a-160d. Accordingly, other than attaching the base 102, the imageable body 104, and the tracking device 150 to the patient 14, the user 22 need not interfere or participate in registration of the patient space to the image space and may efficiently prepare for a procedure, such as a spinal fusion, spinal implant procedure, or the like.

After the registration of the image space to the patient space in block 190, the instrument 90 can be tracked relative to the image data 77. As illustrated in FIG. 5, an icon 90i representing a location of the instrument 90 can be displayed relative to the image data 77 on the display 74. Due to the registration of the image space to the patient space, the position of the icon 90i relative to the image data 77 can substantially identify or mimic the location of the instrument 90 relative to the patient 14 in the patient space. As discussed above, this can allow a navigated procedure to occur.

After registering the image space to the patient space with a first image data set, subsequent image data sets can be acquired. Registration of the patient space to image space can be maintained without additional registration according to the flowchart 170 due to various controls or systems, such as robotic control systems.

For example, the imaging device 12 can know its location when the first image data set of the patient 14 is acquired. Because the imaging device 12 knows its location relative to the patient 12 when the first image data set is registered to the patient space, the registration also generates a known location of the imaging device 12 relative to the patient 14 due to the registration. Accordingly, additional or subsequent image data sets can be acquired of the patient 14 without requiring replacement of the imageable body 104. The position of the imaging device 12 relative to the patient 14 can be used to additionally register the new image data to the patient space. That is, the translation map generated when registering the image space to the patient space in block 190 can also translate the new position of the imaging device 12 relative to the patient 14 when acquiring a second or subsequent data set. Multiple image data sets can, therefore, be acquired of the patient 14 without requiring replacement of the imageable body 104 or further registration using the imageable portions 140a-140d. It will be understood that the imaging device can include the O-Arm® imaging device sold by Medtronic Navigation, Inc. including a robotic system or a position identification system that is operable to substantially precisely know the location of the imaging portions of the imaging device 12.

The imaging device 12, because it knows its location substantially precisely, can be used to register multiple image data sets taken sequentially or at any appropriate time. It will be understood, therefore, that the image data at a first time and a second time need not be separated by a portion of a procedure, but can be used to generate multiple image data sets of the patient 14 one substantially immediately after the other. For example, the imageable body 104 can connected to a portion of the patient 14 that is imaged during a first image data set acquisition time. A second image data acquisition can generate image data of a different portion of the patient 14, substantially immediately after acquiring a first image data set. However, the imageable body 104 need not be moved because the imaging device 12 knows its location during acquisition of the second image data set relative to the first image data set. Accordingly, once registration of the image data and image space to the patient space in block 190 occurs relating to the first image data set, registration of all the subsequent image data sets can be made relative to the image data set that includes the imageable body 104 and the imageable points 140ai-140di. It will be understood, however, the imageable body need not be present in the first or any particular data set. As long as the imageable body is present in one of the image data sets and the position of the imaging device is known for all of the image data sets, all of the image data sets can be registered.

Figure 7:
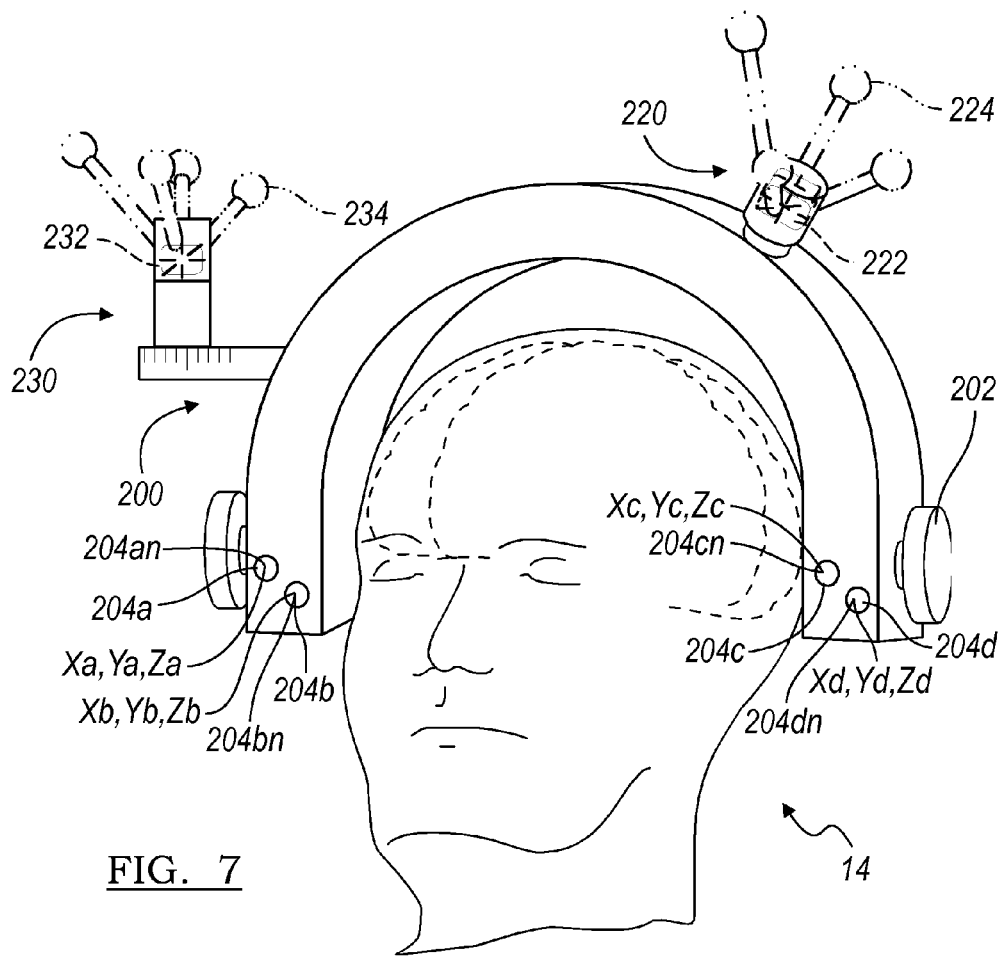
FIG. 7 is a plan view of a patient fixation device with imageable portions.

With reference to FIG. 7, a patient immobilization system 200, such as a Mayfield® clamp, can be connected to the patient 14. The patient immobilization system 200 can be connected to the patient 14 at any appropriate time, such as the prior to acquiring image data of the patient 14. The patient immobilization system 200 can be fixed to the patient 14 and be maintained fixed to the patient 14 during an entire operative procedure, as discussed further herein. The patient immobilization system 200 can be connected to the patient in any appropriate manner, such as with clamps, screws or other connection portions 202.

The patient fixation portion 200 can include a plurality of imageable portions, such as imageable portions 204a-204d. The imageable portions 204a-204d can be imaged with an imaging device, such as the imaging device 12, to generate or include image data that includes image points that represent the locations of the imageable portions 204a-204d. The imageable portions 204a-204d can be similar to the imageable portions 140a-140d, discussed above. The imageable portions 204a-204d included with the patient fixation device 200, therefore, can be imaged with any appropriate imaging system including those discussed above. The imageable portions 204a-204d can also have respective centers 204an-204dn that have three dimensional coordinates Xa, Ya, Za-Xd, Yd, Zd.

The position of the patient fixating device 200 can be determined in patient space with the tracking system, as discussed above. According to various embodiments, a calibration tracking device 220 can be connected to the patient fixation device 200. The calibration tracking device 220 can be tracked with any appropriate tracking system, such as with an EM tracking system via an EM tracking portion 222 or optical tracking system with an optical tracking portion 224. The EM tracking portion 222 or the optical tracking portion 224 can be included in a single device or be provided separately, and used with an appropriate tracking system.

The calibration tracking device 220 can be any appropriate device, such as the trackable tool to selectively touch portions or a trackable fixture that is separately connected with the patient fixation portion 200. According to various embodiments, the calibration tracking device 220 can include a keyed configuration that is positionable relative to the patient fixation device 200 in a selected orientation. A trackable tool (not illustrated) can touch several points to identify a location and orientation of the patient fixation device 200. Because the calibration fixture 220 can be keyed to the patient fixture 200 its orientation is known relative to the fixture 200 and the imageable portions 204a-204d. In addition, the patient fixation device 200 can transmit its location in the image data. For example, the patient fixation device 200 can include a member or device that can transmit to a magnetic resonance imager (MRI) its location within the image data to identify the location of the imageable portions 204a-204d.

When the calibration tracking device 220 is interconnected with the patient fixation portion 200, the navigation system 10 can know the location of the imageable portions 204a-204d in the patient space. This allows the navigation system to know the locations of the imageable portions 204a-204d that generates the image data points 204ai-204di, illustrated in FIG. 8, in the image data 77'. Once the location of the patient fixture 200 is known, the calibration fixture 220 can be removed. The image data 77' can be acquired with any appropriate image device, such as the imaging device is discussed above. Similarly the image data 77 can be displayed on the display 74 discussed above.

In addition to, or alternative to the calibration tracking device 220, a patient tracking device or dynamic reference frame (DRF) 230 can be interconnected with the patient fixation device 200. The dynamic reference frame 230 can be interconnected with the patient fixation device 200 to track motion of the patient 14 prior to and during an operative procedure. The DRF 230 is fixed to the fixation device 200 which is, in turn, fixed to the patient 14. Accordingly, movement of the patient 14 is translated through the patient fixation device 200 to the dynamic reference frame 230.

The dynamic reference frame 230 can be tracked with a tracking system, as discussed above, such as via an EM tracking portion 232 or one or more optical tracking portions 234. The DRF 230 can be used to maintain a registration of image space to patient space, as discussed above, in a navigation system. Accordingly, once registration occurs between the patient space of the patient 14 and image space of the image data, the DRF 230 can assist in maintaining the registration.

In addition, the dynamic reference frame 230 can be tracked relative to the imageable portions 204a-204d. The imageable portions 204a-204d can be positioned at a fixed or selected location relative to the DRF 230.

Figure 8:
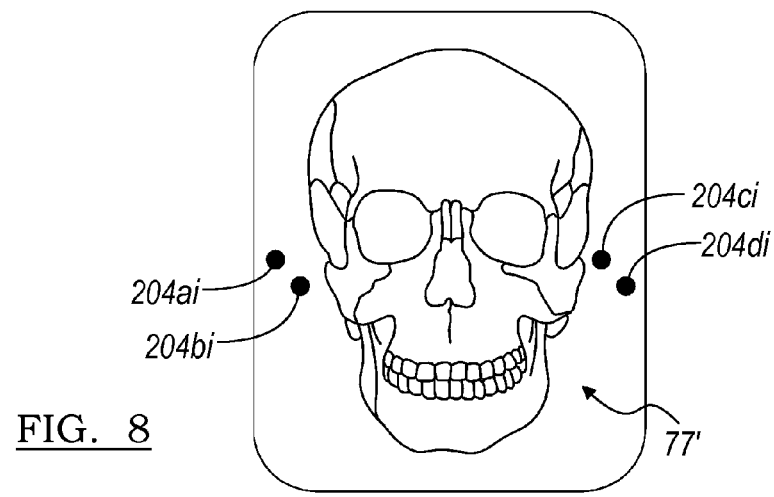
FIG. 8 is a diagram of image data.

Because the DRF 230 is fixed to the patient fixation device 200, the location of the imageable portions 204a-204d can be known. Similarly, because the DRF 230 can be tracked with a tracking system, the physical location of the imageable portions 204a-204d can be known relative to the patient space of the patient 14. In addition, when the imageable points 204ai-204di are identified in the image data, as illustrated in FIG. 8, the image space location of the points can be translated to the physical location of the imageable portions 204a-204d.

According to various embodiments, the patient holder 200 that includes the imageable portions 204 and the two tracking devices 220 and 230 can be used and configured in selected variations. For example, the tracking device 220 affixed to the patient holder 200 can be used to determine the orientation of the imaginable portions 204 in patient space, as discussed above. The DRF 230 can then be attached to the patient holder 200 in any appropriate manner which can be moveable and selectively fixable, such as with locking clamps, relative to the patient 14. Accordingly, the navigation system 10 can take a single or initial snapshot to determine an orientation of the DRF 230 relative to the tracking device 220 and from this determine the orientation or position of the imageable portions 204 relative to the DRF 230. After the snapshot, at least one of the DRF 230 or the tracking device 220 can be removed from the patient holder 200. For example, if the tracking device 220 is not in a convenient location or would be covered with surgical draping, the tracking device 220 can be removed once the DRF 230 is fixed relative to the patient 14. In addition, it would be understood that the tracking device 220 can be positioned in a repeatable and removable manner. For example, a linkage system can be used to interconnect the tracking device 220 with the patient holder 200 such that the position of the tracking device 220 is known relative to the patient holder 200. Accordingly, the tracking device 220 can be used as the DRF 230 to position the tracking device 220 in the convenient location even with surgical draping. Accordingly, it will be understood that the patient holder 200 including the imageable portions 204 can be used with one or two tracking devices, such as the tracking device 220 and the DRF 230, as discussed above.

Registration of the image space and the image data 77 and patient space of the patient 14 can be performed substantially similarly as discussed in the method 170 illustrated in the flowchart in FIG. 6. The location of the imageable points 204ai-204di can be determined substantially automatically. Similarly, the known position of the physical location of the imageable portions 204a-204d can be known to either or both of the tracking devices 220, 230. Accordingly, the system can know the physical location of the imageable portions 204a-204d for registration to the image points 204ai-204di.

The base 102 or the patient fixation device 200 can be positioned or fixed relative to the patient 14 during a procedure. Appropriate bases or fixation portions can be fixed to any appropriate subject, such as a work piece, during a procedure or imaging of the subject. The imageable portions, either connected to or integrated with the base or fixation device, can be imaged in the image data. Because the tracking device, such as the tracking device 150, the calibration device 220, or the DRF 230, can be connected with the base or fixation device the location of the imageable portions on the base or fixation device can be known throughout the procedure. Accordingly, by maintaining fixation of the base 102 or the fixation device 200 to the patient or subject and tracking or knowing the location of the imageable portions in the subject space, a re-registration need not be performed. The registration can be maintained by maintaining a fixation of the base 102 or patient fixation device 200 to the patient 14. This can make a procedure more efficient by eliminating or reducing the need to register or identify locations of imageable portions in the image data 77.

As discussed above, imageable portions can be imaged with the imaging device 12. The imaging device 12 can be appropriate types of imaging devices having selected features as discussed herein. The imageable portions, including the imageable spheres 140a-140d, can be displayed or found in the image data as points or dots as 140ai-140di exemplarily illustrated in FIG. 5. As discussed herein, the image points 140Ai-140di are image fiducial features that can be used for coordination with fiducial features of a model of the fiducial assembly and/or registration of the image space to the patient space. The system or method for registering the subject space, which can include the patient space, to the image space is illustrated in FIG. 6.

According to various embodiments, however, while acquiring image data of the subject to which the imageable portions are affixed or connected an appropriate or required amount of image data relating to the imageable portions, such as the imageable fiducial portions 140a-140d, may not or need not be present. For example, a three dimensional reconstruction of the imageable portions or a fiducial assembly including the imageable portions may not be possible after acquiring a plurality of two dimensional (2D) x-ray projections. Nevertheless, using various image merging and/or registration techniques a registration is still possible between the subject space (defined by the subject or object) and the image space (defined by image data including a three dimensional reconstruction based on two dimensional projections, such as 2D x-ray projections).

According to various embodiments, and as exemplary discussed herein, image data of at least three different imageable fiducial portions 140a-140d may be required for a registration. The image data of the three fiducial portions can also be referred to as image fiducial features. The image fiducial features can be the image data that can be identified by a human user and/or a computer system (e.g. executing instructions related to an algorithm) as at least a portion of the fiducial that is imaged in the image data. Further, the acquired 2D x-ray projections can be acquired at selected angular offsets or differences (e.g. about 5-15 degrees apart, including at least 10 degrees apart) relative to one another to allow for a selected accurate registration and 3D reconstruction. It will be understood, however, that lesser degrees of offset between image data sets (e.g. less than about 10 degrees) can be used depending upon the desired, selected, or required degree of accuracy in the registration and reconstruction. In theory, a very small angular difference could be used if a large registration error is acceptable. Furthermore, depending on the shape of the fiducial assembly, in theory it is possible to estimate the registration from a single 2D image.

Although, according to various embodiments, identifying or determining at least three fiducial features to be points can be used for coordination and registration of the image space to the subject space. For example, three discrete points can be used for registration. As discussed herein, less than three or a different type or amount of image fiducial features can be obtained depending upon the registration accuracy and/or type or design of fiducial assembly. For example, a single fiducial feature can include a geometric shape or line that can be used for registration or coordination.

Image data acquired of the subject, including the patient 14, can include x-ray image projections, as discussed further herein. Briefly, the 2D x-ray projections can be image data acquired by emitting x-rays from a source and detecting them with a detector. Generally a plurality of these 2D images can be acquired, but all of the images or projections are 2D. A three-dimensional (3D) reconstruction can be made of the imaged object based on the plurality of 2D projections, as long as enough of the subject is appropriately images in the 2D projections. The amount, number, special distance, etc. of the 2D images required for a 3D reconstruction can differ depending upon the algorithm used for reconstruction, quality of the 3D model required, etc.

Figure 9A:
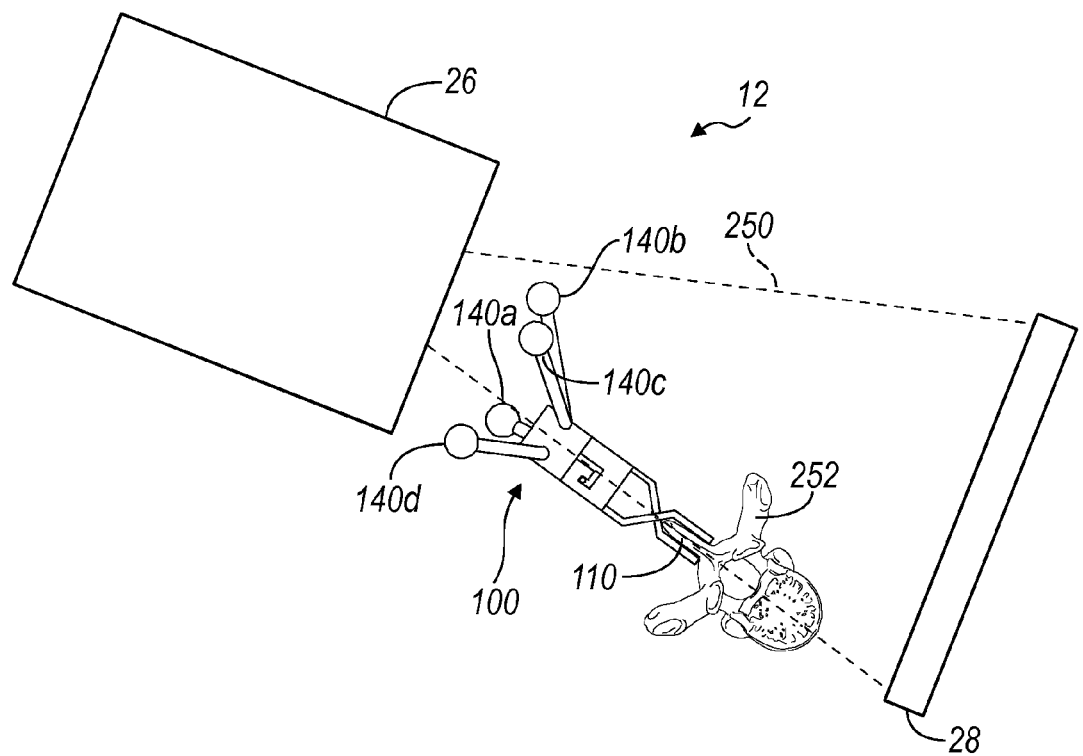
FIGS. 9A-9C are a plurality of schematic environmental views of an imaging system and an imageable fiducial array.
Figure 9B:
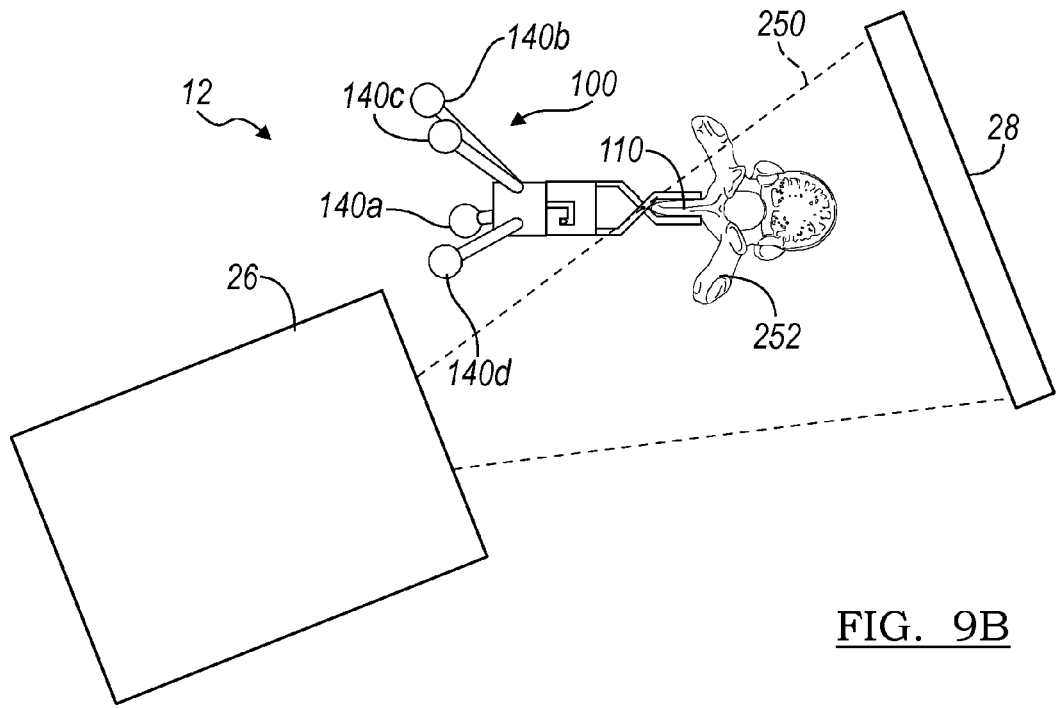
Figure 9C:
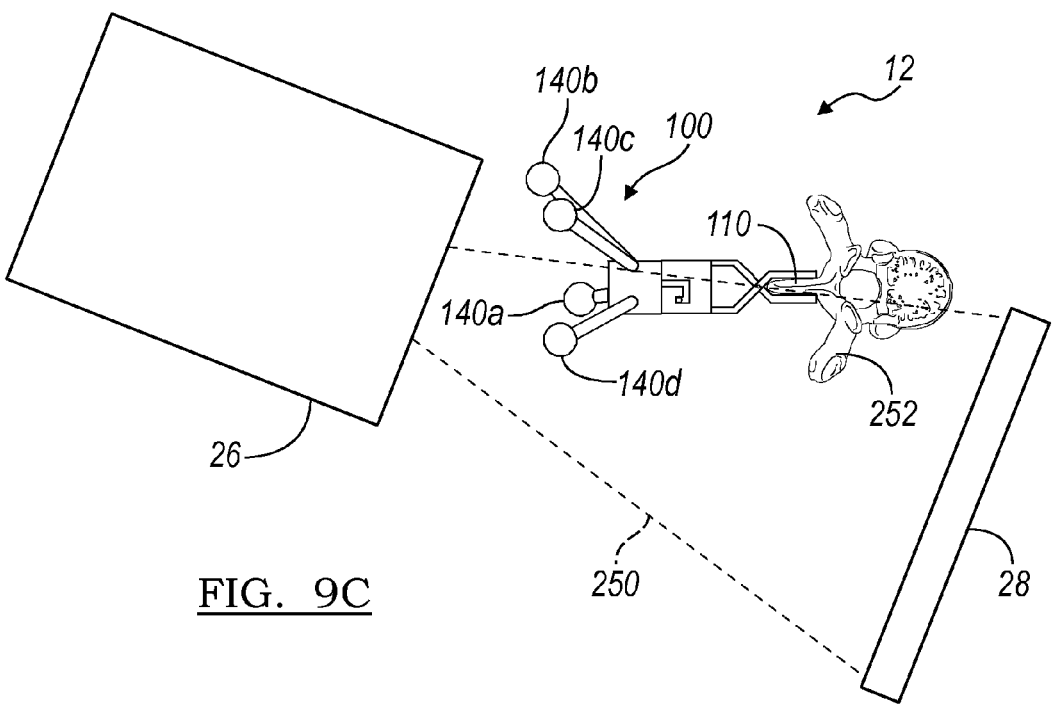

The imaging device 12, as schematically illustrated in FIGS. 9A-9C, can include the x-ray source or emission portion 26 and the x-ray receiving or imaging receiving portion 28. The source 26 can emit a cone of x-rays generally outlined as the x-ray cone 250 illustrated in FIGS. 9A-9C. The x-ray cone 250 can be emitted from the source 26 of an appropriate imaging device that can be precisely positioned relative to the subject 14 such as the exemplary vertebrae 252 of the spine 108.

Figure 10A:
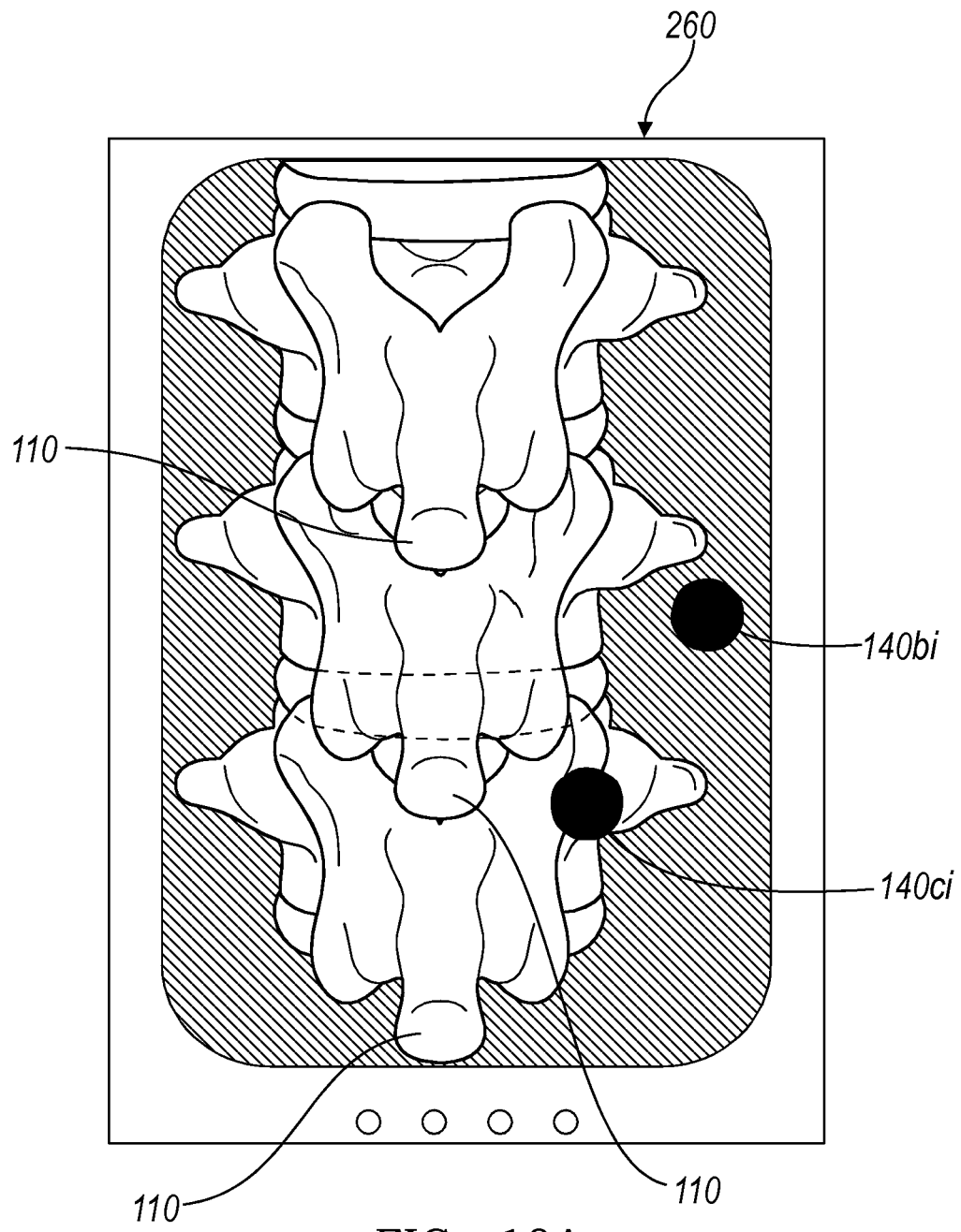
FIGS. 10A-10C illustrates a plurality of two-dimensional x-ray projections respectively relating to FIGS. 9A-9C.
Figure 10B:
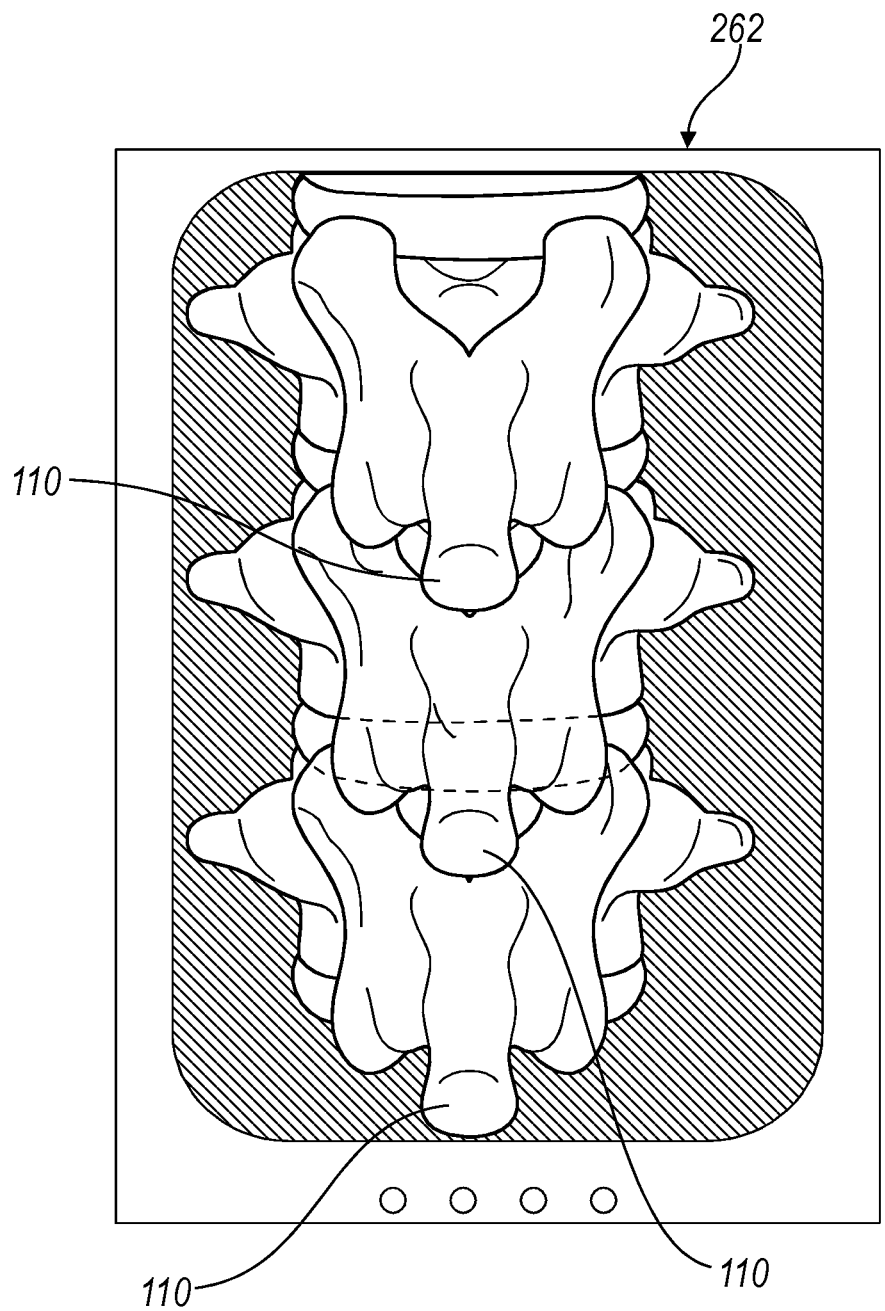
Figure 10C:
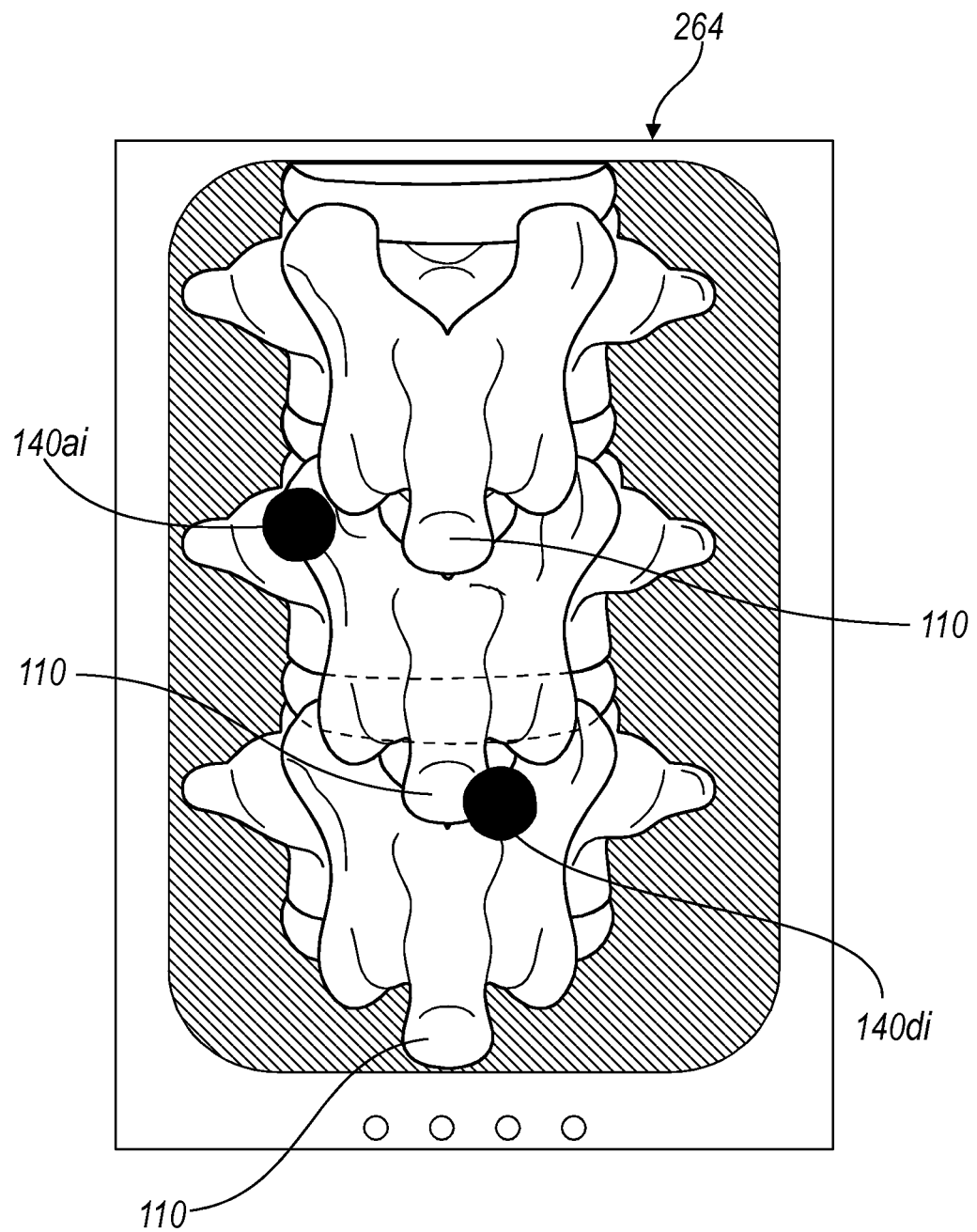

Generally, the imaging device can be positioned at known parameters, as discussed below, relative to the subject 14. The image data, including the x-ray projections, can then be acquired at the known parameters relative to the patient 14. Parameters of the imaging device can include a position of the emission portion 26 and the x-ray receiving portion 28. In other words, the imaging system 12 can move relative to the object, including the patient 14, to be imaged. In the FIGS. 9A-9C the emission portion 26 and the x-ray receiving portion 28 are positioned at three different positions relative to the object to be imaged, such as the vertebrae 252 and the fiducial assembly 100. As the emission portion 26 and the x-ray receiving portion 28 move a position parameter changes and different 2D projections are acquired. Different 2D projections 260, 262, and 264 are schematically illustrated in FIGS. 10A-10C relating to FIGS. 9A-9C, respectively.

The imageable fiducial device 100 can be connected to the spinous process 110 of the vertebrae 252 such that at least a portion of the imageable fiducial device 100 appears in at least a selected number of the x-ray projections generated with the imaging device 12. As illustrated in FIGS. 10A-C, a series of x-ray projects can be acquired of the spine 108 including the vertebra 252. As illustrated in FIGS. 10A-C, the series of x-ray projections can include a first x-ray projection 260 (schematically illustrating the position parameters in FIG. 9A), a second x-ray projection 262 (schematically illustrating the position parameters in FIG. 9B), and a third x-ray projection 264 (schematically illustrating the position parameters in FIG. 9C). Each of the x-ray projections 260-264 are acquired with the imaging device at different position parameters (e.g. angle, distance) relative to the vertebra 252.

Although each of the projections 260, 262, 264 includes the vertebrae, only the exemplary projections 260 and 264 include a portion of the imageable fiducial marker device 100. For example, the x-ray projection 260 includes only two of the imageable portions, exemplarily illustrated as imageable portions 140bi and 140ci relative to an image projection of the vertebrae 252i. The second x-ray projection 262 includes an image of the vertebrae 252i, but does not include any image data relating to the imageable portions 140. Finally, the third projection 264 includes image data of the vertebra 252i and image data of two different imageable portions, exemplary illustrated as 140ai and 140di. Thus, although the imaging device 12 can acquire a plurality of x-ray projections of the vertebra 252, only a sub-plurality of the x-ray projections may include image data relating to the imageable portions 140 of the fiducial assembly 100.

When attempting to register the navigation system 10 relative to the patient 14 to register the subject space to the image space, various comparisons may be selected to register and generate a translation map between the image space and the patient space. The processor system 72 (or any other appropriate processing system which can include a separate physical computer processor) can then execute instructions to both identify the x-ray projections with image data relating to the imageable portions 140 and can identify the imageable portions 140i in the x-ray projections. Alternatively, the user 81 can both identify the imageable portions 140i in the x-ray projections and which of the plurality of x-ray projections has image data relating to the imageable portions.

Figure 11:
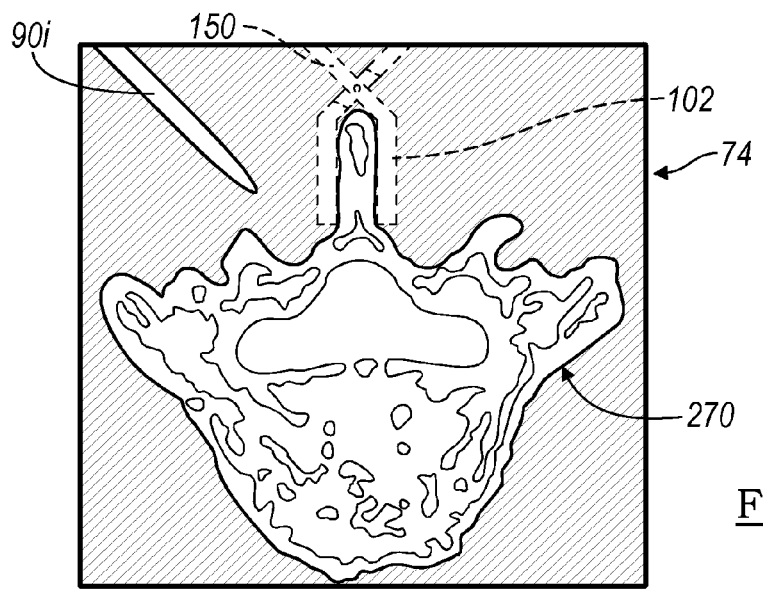
FIG. 11 is a plan view of a display device illustrating image data and an icon of a tracked instrument.

The imaging system 12 can be used to acquire all image data of the patient 14 for an operative procedure. Accordingly, the imaging device 12, such as the O-Arm® imaging device and other selected imaging devices, can be used intra-operatively (i.e. in an operating room/theater once the patient 14 is prepared for a surgical procedure) to acquire all image data of a patient 14 to allow for navigation of a procedure relative to the patient 14. In acquiring image data for whatever reason (e.g. radiation exposure of the patient 14, time of image acquisition, etc.), the entire fiducial assembly 100 may not be imaged in the image projections of the patient 14, at least for an appropriate or complete three dimensional reconstruction. Although the vertebrae 252, or other selected portions of the anatomy of the patient 14, can be appropriately imaged to allow for a three dimensional reconstruction 270, as illustrated in FIG. 11. If the fiducial assembly, including at least the imageable portions 140, are not imaged enough for a three dimensional reconstruction then registration of the subject space to the image space, including the three dimensional reconstruction image space 270, may be limited or impossible due to the lack of acquiring an appropriate amount of image data relating to the fiducial assembly 100 in each of the x-ray projections 260-264. Accordingly, alternative registration or matching systems can be used.

Briefly, it will be noted that any appropriate number of x-ray projections can be collected or acquired and the three x-rays projections 260-264 are merely exemplarily. Also, the three dimensional reconstruction of the subject space, including the vertebrae, can be based on selected algorithms. For example, a three dimensional or volumetric reconstruction can include appropriate algebraic techniques such as Expectation maximization (EM), Ordered Subsets EM (OS-EM), Simultaneous Algebraic Reconstruction Technique (SART) and Total Variation Minimization (TVM), as generally understood by those skilled in the art. The application to performing a 3D volumetric reconstruction based on the 2D x-ray projections allows for efficient and complete volumetric reconstruction of the imaged object. Generally, an algebraic technique can include an iterative process to perform a reconstruction of the patient 14 or other object for display.

The 3D reconstruction can be then be displayed as the image data. For example, a pure or theoretical image data projection, such as those based on or generated from an atlas or stylized model of a "theoretical" patient, can be iteratively changed until the theoretical projection images match the acquired 2D projection image data of the patient 14. Then, the stylized model can be appropriately altered as the 3D volumetric reconstruction model of the acquired 2D projection image data of the selected patient 14 and can be used in a surgical intervention, such as navigation, diagnosis, or planning. The theoretical model can be associated with theoretical image data to construct the theoretical model. In this way, the 3D reconstruction model can be displayed as the image data and is generated based upon image data acquired of the patient 14 with the imaging device 12. The 2D x-ray projection image data can be acquired by moving the imaging device 12, such as the source 26 and receiver 28, relative to the patient 14. The movement can be substantially annular or 360° orientation movement of the source/detector around the patient 14, partial annular motion, or other motion to allow for acquisition of a plurality of 2D x-ray projections from a plurality of positions relative to the patient 14.

The three dimension reconstruction 270 can be displayed on a display, such as the display 74, can be further superimposed with an illustration of an instrument icon 90i relative to the three dimension reconstruction 270. To appropriately illustrate the instrument icon 90i relative to the three dimensional reconstruction 270 of the patient 14 registration of the subject space to the image space may be required. The registration allows a translation map can be generated between the subject space and the image space.

To allow for the appropriate registration, the x-ray projections including an appropriate amount of image data regarding the fiducial assembly 100 can be used to merge or register the three dimensional reconstruction 270 (based on the x-ray projections) to selected ones of the x-ray projections to register the x-ray projections to the three dimensional reconstruction 270. Once the x-ray projections are registered to the three dimensional reconstruction 270 a registration or translation map can then be made to the subject space based on the known position of the fiducial assembly in the x-ray projections (as discussed herein based on imaging device parameters and synthetic digital radiograph reconstructions) and the parameters of the imaging device 12.

The merging or registration of the selected x-ray projections to the three dimensional reconstruction 270 can be similar to two dimensional to three dimensional registration as disclosed in U.S. Pat. No. 7,570,791, incorporated herein by reference. Generally, and discussed in greater detail below, the x-ray projections of the vertebrae 252, including the fiducial assembly 100, having an appropriate amount of image data of the fiducial assembly 100 can be registered to a synthetic digital radiograph reconstructions (SDRR) of the fiducial assembly 100 to allow for a registration of the subject space to the image space of the three dimension reconstruction 270. Generally, it can be selected acquire or have x-ray projections of at least three imageable members for registration purposes. Thus, an appropriate number of x-ray projections may include a number of x-ray projections that include at least three different imageable portions 140 of the fiducial assembly 100. It is understood, however, that other appropriate amounts of fiducial image data can be used as discussed herein.

As used herein a synthetic digital radiograph reconstruction (SDRR) of the fiducial assembly 100 is based on a three dimensional model, including a digital model, of the fiducial assembly 100 from which a two dimensional reconstruction is made that mimics or includes information similar to a two dimensional digital radiograph of the fiducial assembly 100. The configuration of the fiducial assembly 100 (e.g. a computer aided design model or other three dimension digital model) can be used in combination with the intrinsic and extrinsic parameters (e.g. orientation, position, etc of the imaging device 12) to generate the SDRRs that can be registered to the selected x-ray projections. Generation of the SDRR can be similar to the generally known techniques of generating digital radiograph reconstructions of image data acquired of various subjects.

Figure 12:
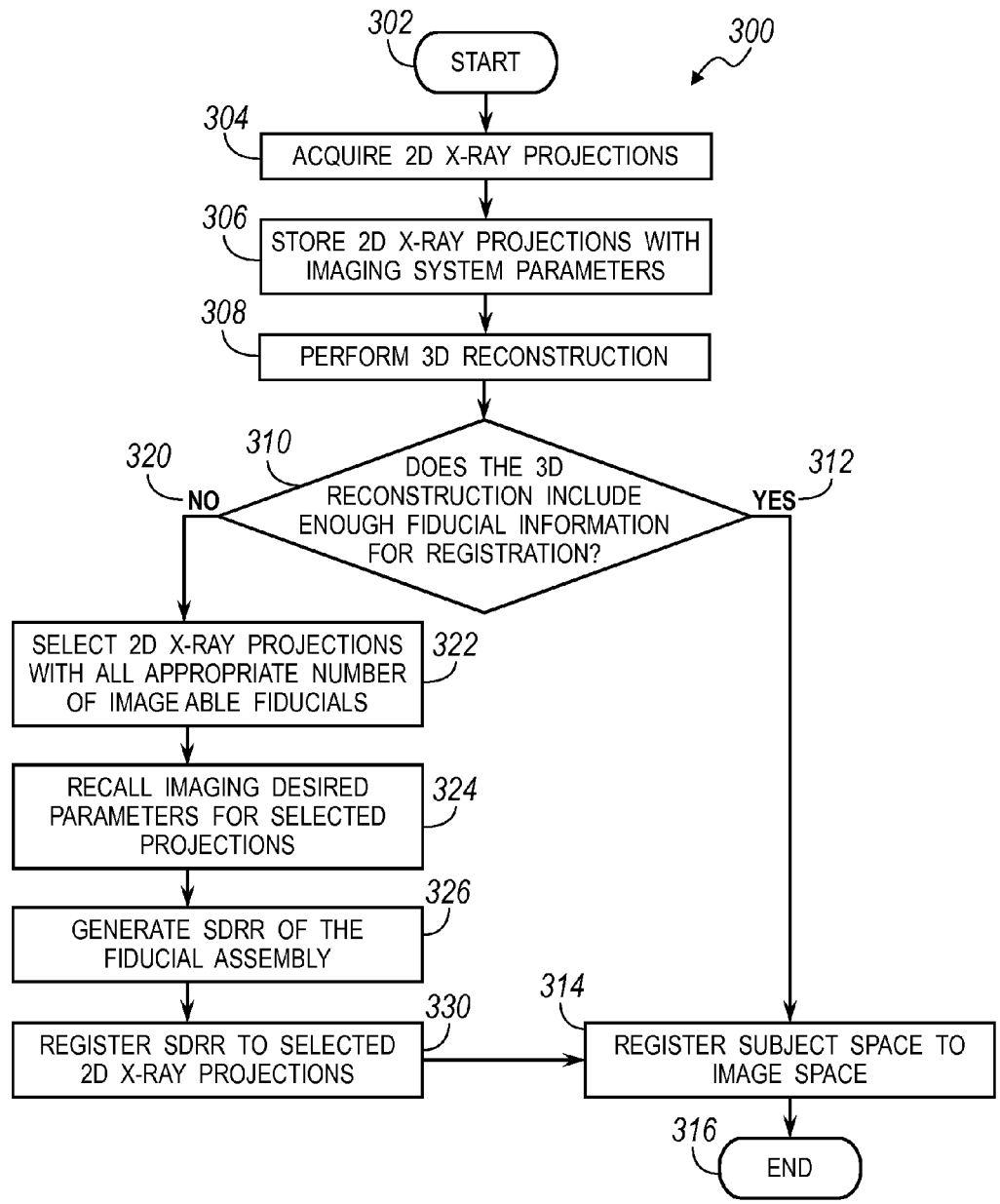
FIG. 12 is a flow chart of a method of registering a first set of image data to a second set of image data.

With reference to FIG. 12, and continuing reference to FIGS. 1-11, a flowchart 300 illustrates a process of registering at least the two dimensional x-ray projections 260 and 264 that include image data of the fiducial assembly 100 to the three dimensional reconstruction 270. The flowchart 300 illustrates an exemplary method to allow for registration of patient space or subject space to the image space. It will be understood that although all the discussion is related more specifically or more directly to registering subject space to image space when a fiducial assembly is not completely imaged for reconstruction in the three dimensional reconstruction, that the following process can also be used to either enhance, supplement, or otherwise assist in a registration even when a fiducial assembly is imaged completely enough for three dimensional reconstruction. Further, it is understood that the following method can be implemented as an algorithm that is encoded in instructions that can be executed by the processor 72, or an appropriate processor system (e.g. a computer processor system) to perform the registration.

The flowchart 300 begins in start block 302 and then progresses to acquiring image data of the subject including two-dimensional (2D) x-ray projections with the imaging system 12 in block 304. The acquired 2D x-ray projections can be acquired with the imaging system 12 discussed above. Particular imaging systems can include the O-Arm® Imaging System that can acquire 2D x-ray projections at substantially precisely known and repeatable locations relative to the patient 14. Although the imaging system 12 need not require repeatable location imaging, the imaging system 12 is generally able to determine and/or store imaging system parameters, as discussed herein. The image data can be acquired during an operative procedure or immediately prior to an operative procedure and in an operating room. Thus, the image data can be acquired relative to the patient 14 at a substantially known location relative to the patient 14 based on tracking the imaging device with the tracking device 37 or by information in the controls of the imaging device 12. Also, the fiducial assembly 100 can be affixed to the patient 14 and remain in place during the image data acquisition.

Generally, appropriate imaging systems will allow for the acquisition of an appropriate number of 2D x-ray projections to allow for a three dimension (3D) reconstruction of the selected and imaged portion of the subject 14, such as the vertebrae 252. The imaging system 12 generally will allow for the determination or knowledge of parameters of the imaging system 12 relative to the patient 14. Imaging parameters can include extrinsic parameters such as a position of the imaging system 12 relative to the patient 14. The position of the imaging system 12 relative to the patient 14 can include the position of the x-ray source 26 and the position of the x-ray receiver 28 relative to the patient 14 and fiducial assembly 100. The position of the imaging device 12 relative to the patient 14 can be known based upon the known positioning of the imaging device 12 relative to the patient such as with a mechanical positioning mechanism associated with the imaging device 12. Alternatively, or in addition thereto, the tracking device 37 can be used to track the location of the image device 12 relative to the patient 14. Regardless, the position of the imaging device 12 relative to the patient 14 can be determined and be saved with a memory system, such as in the controller, as an extrinsic parameter. Intrinsic parameters can include geometry of the imaging device (e.g. annular), a position of the source 26 relative to the x-ray receiving section 28, and other intrinsic parameters relating to the internal function of the imaging device 12 including x-ray energy parameters and the like.

After the 2D x-ray projections are acquired in block 304, the 2D x-ray projections can be stored in block 306 with the appropriate imaging system parameters, including those discussed above. Each of the 2D x-ray projections can include specific and unique imaging system parameters, such as the position of the imaging system relative to the patient 14, that relate to each 2D x-ray projection. Accordingly, each of the 2D x-ray projections can be saved with the related imaging system parameters in block 306. The appropriate number of x-ray projections required to be acquired of the patient 14 can vary and depend upon the portion of the anatomy to be operated on, such as the vertebrae 252, to allow for a 3D reconstruction using the stored 2D x-ray projections.

Once an appropriate number of 2D x-ray projections are acquired, a 3D reconstruction can be performed in block 308. The 3D reconstruction can be performed to reconstruct a 3D image of the portion of the anatomy, such as the vertebrae 252, from the 2D x-ray image projections. The 3D reconstruction 270 can then be displayed on the display device 74.

To perform the 3D reconstruction from the 2D image x-ray projections appropriate algorithms can be executed by a processor system, including the processor of the navigation system 10, to generate the 3D reconstruction. Appropriate algorithms can include those discussed above. Accordingly, the 3D reconstruction can be substantially automatically performed or reconstructed from the 2D image x-ray projections based upon stored and executed software programs and algorithms.

Once the 3D reconstruction is completed, a decision block 310 can be entered to determine whether the 3D reconstruction includes enough fiducial information for registration. The appropriate amount of fiducial information can include whether the entire fiducial assembly 100, or at least the imageable fiducial portions 140*a*-140*d* are all present or identifiable in the completed 3D reconstruction in block 308. If all or an appropriate minimum number (e.g. three of the imageable portions 140*a*-140*d*) of the fiducial imageable portions 140*a*-140*d* can be identified in the 3D reconstruction, then an appropriate amount of fiducial information is present in the 3D reconstruction and the YES path 312 can be followed to register the subject space to the image space in block 314. As discussed above, once the image space is registered to the subject space then a translation map from the subject space to the image space can be determined and the navigated procedure can occur. During the navigated procedure illustrations of the location of the instrument 90 relative to patient 14 can be illustrated with the instrument icon 90*i* relative to the three dimensional reconstruction of the patient 270, as illustrated in FIG. 11. The registration procedure 300 can then end in block 316.

Alternatively, if all or not enough of the imageable portions 140 (e.g. less than three or an amount for registration) are not identifiable in the 3D reconstruction 270, then the decision block 310 can follow the NO path 320 to generate an appropriate registration of the subject space to the image space. In following the NO path 320, the navigation system 10, either alone or with input from the user 81, can identify and select 2D x-ray projections that are stored in block 306 that include image data of the imageable fiducials 140 in block 322. The imageable fiducials 140 on the fiducial assembly 100 can be imaged in only a sub-plurality of the x-ray projections are acquired in block 304. Although the fiducial assembly 100 may not be imaged completely or enough to allow for an appropriate 3D reconstruction of the fiducial assembly 100 in block 310, each of the x-ray projections or a selected number of the x-ray projections acquired in block 304 can include at least one of the imageable fiducials 140*a*-140*d*. The selected x-ray projections including image data of the imageable portions 140*a*-*d* can include all or a selected number of the sub-plurality of the x-ray projections including image data of the imageable portions 140*a*-*d*.

All or a selected number of the 2D x-ray projections are selected that include all or only an appropriate number of the imageable fiducials 140 in block 322. For example, all of the sub-plurality of the x-ray projections including image data of the imageable portions 140*a*-*d* can be the selected 2D x-ray projections. An appropriate number can include a number that will allow for registration of the image space to the patient space. For example, three of the imageable fiducials 140 imaged in the acquired 2D x-ray projections in block 304 may be enough to allow for an appropriate registration. It can be selected, however, to include at least 4, 5, or any appropriate number of the imageable fiducials that are included with the fiducial assembly 100. Additionally, it will be understood that additional images or projections can be acquired with the imaging device 12 to ensure the appropriate number of the imageable fiducials 140 are imaged in the x-ray projections. Thus, if the 2D x-ray projections from block 304 do not include enough of the imageable fiducials, the imaging device 12 can be repositioned relative to the patient 14 and the fiducial assembly 100 to acquire additional projections to allow for an appropriate registration.

After selecting an appropriate number of the 2D x-ray projections in block 322, the parameters relating to the selected 2D x-ray projections can be recalled in block 324 that were stored in block 306. The imaging device parameters can be those discussed above, including the position of the imaging device 12 relative to the patent 14 or the fiducial assembly 100 during imaging of the subject and acquiring the 2D x-ray projections selected in block 322. After recalling the imaging device parameters in block 324, synthetic digital radiograph reconstructions (SDRR) of the fiducial assembly 100 can be generated.

Figure 13:
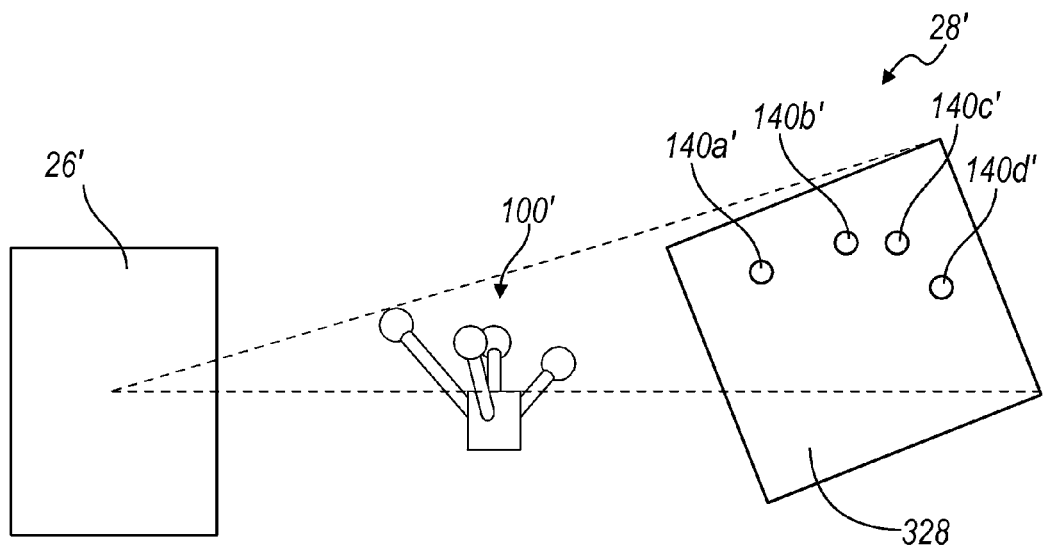
FIG. 13 is a schematic illustration of generating a SDRR or acquiring two-dimensional x-ray projections of a fiducial assembly, according to various embodiments.

With reference to FIG. 13, a digital three dimensional model 100' of the fiducial assembly 100 can be stored. The digital three dimensional model 100' of the fiducial assembly 100 can include a computer aided design (CAD) model or computer generated model of the fiducial assembly 100. The digital 3D model 100' includes information regarding the locations, including relative locations of the imageable fiducial portions 140. The information can include relative positions of fiducial features of the fiducial assembly 100. For example, the fiducial assembly 100 is imaged and the imageable fiducial portions 140 appear in the image. The feature used for registration (i.e. the image fiducial feature) can include a determined center point of a portion of the image data relating to the imageable fiducial portion 140. Thus, the center of the imageable fiducial portion 140 in the 3D model 100' and their determined locations can be the fiducial features that can be used to coordinate with the image fiducial features.

According to various embodiments, the digital three dimensional model of the fiducial assembly 100 can then be used to generate one or more of a SDRR 328 or other representation of the fiducial assembly regarding the 3D or 2D position, including relative positions, of fiducial features of the fiducial assembly. The SDRR 328 can be generated using the imaging device parameters, including the location of the x-ray source 26' and the x-ray receiving section 28'. The SDRR 328 is a two dimensional projection of the digital three dimensional model 100' based on the imaging device parameters and/or other selected parameters.

The SDRR 328 is generated to include the imageable fiducial portions 140*a*'-140*d'* as if the imageable fiducial assembly 100 were imaged with the imaging device 12 from the source 26 to the x-ray receiving section 28. Briefly, the SDRR 328 can be generated using the model 100' based upon the imaging device parameters recalled in block 324. That is, the three dimensional position of the imaging source 26 relative to the receiving portion 28 and the fiducial assembly 100 in the subject space is used to mimic an orientation of the imaging source 26' and the receiving section 28' to generate the SDRR 328. An extensive discussion of digital radiograph reconstructions of three dimensional reconstructions is described in U.S. Pat. No. 7,570,791, incorporated herein by reference. Appropriate processes can be used to form the SDRR 328, including algorithms encoded as instructions to be executed by the processor 72 or other separated processor system (e.g. a separate computer processor).

Generating the SDRR 328 of the model 100' can be substantially similar to generating a digital radiograph reconstruction of a three dimensional reconstruction, but the SDRR 328 is generated using the three dimensional model 100'. In generating the SDRR 328 all of the imageable portions 140*a*-*d* can be reconstructed in the SDRR 328 as the fiducial features 140*a*'-140*d'*. Generally, the fiducial features, which are based on determined positions of the imageable fiducial portions 140*a*-*d* in the 3D model 100', represent imaged imageable fiducial marks 140*a*-*d*. The fiducial features 140*a*'-140*d'* relate to the portion used for registration, which can be the determined center of a circle or sphere, a surface, etc. Thus, although the parameters of the imaging device are used to determine the appropriate orientation for generating the SDRR 328 all of the fiducial information can be placed in the SDRR 328 due to its synthetic nature and being able to place the source 26' at any distance relative to the three dimensional model 100' while maintaining a selected orientation (e.g. one based on the imaging device parameters) relative to the receiving section 28'

A plurality of the SDRRs 328 can be generated and used to match or merge with the selected 2D x-ray projections from block 322 to generate a registration. For example, as illustrated in FIGS. 10A-10C, a plurality of the 2D x-ray projections can include image data or images of the fiducial imageable fiducial portions, such as exemplary x-ray projections 260 and 264. Thus, one or more SDRRs 328 can be generated based on the imaging device parameters for each of the selected x-ray projections, such as the two x-ray projections 260 and 264. Each of the SDRRs 32 relating to the different x-ray projections will have different positions of the imageable fiducial portions 140a'-140d' based on the parameters of the imaging device. This is due to the 3D nature of the fiducial assembly 100 and its related three dimensional model 100' and the differing perceptive of the imaging device 12 relative to the fiducial assembly 100 and its related three dimensional model 100' in each of the x-ray projections. The selected x-ray projections including the imageable fiducial portions, such as those selected in block 322, can be matched to the respective SDRRs 328.

The registration of the SDRRs to the selected 2D x-ray projections occurs in block 330. The registration of the SDRRs to the selected 2D x-ray projections allows for the generation of the translation map of the subject space to the image space in block 314. The registration of the SDRRs to the 2D x-ray projections and the generation of the subsequent translation map is similar to the two dimensional to three dimensional image registration as disclosed in U.S. Pat. No. 7,570,791, incorporated herein by reference. Generally, the SDRR includes parameters or the geometry of the fiducial assembly 100 based upon the fiducial assembly model 100' that is identical to the fiducial assembly 100. The fiducial assembly model 100', therefore, can be used to generate the SDRR 328 that would be substantially identical to the 2D x-ray projection through the fiducial assembly 100 if generated in the subject space. Accordingly, the two dimensional SDRR of the model 100' can be used to identify the orientation of the fiducial assembly 100 in the three dimensional reconstruction 270.

In other words, when generating the SDRR 328 to substantially match the imageable fiducial portions 140 in the selected x-ray projection in block 322, a known orientation of the imageable fiducial portion 100 relative to the imaging device 12 is determined when the SDRR 328 matches the imaged portion in the selected two dimensional projections in block 322. Knowing the three dimensional orientation of the fiducial assembly 100, relative to the imaging device, such as to generate the appropriate SDRR 328, allows for determining an orientation of the fiducial assembly 100 or an appropriate portion of the fiducial assembly, such as the connecting base 102, to the anatomy of the patient 14. As illustrated in FIG. 11, by knowing the appropriate orientation of the three dimensional fiducial assembly 100 relative to the vertebrae 252, the orientation of the base 102 relative to the three dimension reconstruction 270 can also be determined. As discussed above, this can allow for registration of the subject space to the image space for registering or maintaining registration of the patient to the image data and for performing the selected navigated procedure. Accordingly, three dimensional subject space can be registered to the three dimensional reconstruction 270 of the image data space even if the acquired 2D x-ray projections do not include enough image data to allow for a 3D reconstruction of the fiducial assembly 100 with the other imaged portions.

While the SDRR 328 can be generated to include the fiducial features 140a'-140d', it will be understood that the known geometry of the 3D model 100' can be used alone to determine the positions of the fiducial features 140a'-140d' in absolute position and relative to position to one another. For example, rather than generating the SDRR 328 of the 3D model 100', the spatial relationships of the imageable fiducial portions 140a-140d in the model 100' can be determined directly from the model. That is, each of the imageable fiducial portions 140a-140d has a 3D position relative to one another that is known based upon the 3D model 100'. Accordingly, a two dimensional position of the fiducial features, based upon the imageable fiducial portions 140a-140d can be determined without generating a complete synthetic digitally reconstructed radiograph of the model 100'. It will be understood that similar information can be determined based upon the 3D model 100' using the known spatial relationships of the imageable fiducial portions 140a-140d in the model 100' thus generating the SDRR 328 is not necessary to determine the positions of the fiducial features that are based on the imageable fiducial portions 140a-140d. Additionally, as discussed further herein, any appropriate geometry of a fiducial assembly that can be modeled can be used to generate or determine the positions of fiducial features rather than including a plurality of the fiducial portions 140a-140d (e.g. curved or intersecting rods, non-spherical geometric elements, etc.).

It will be understood that more than one processor system, including a computer processor, can be used as the various disclosed processor systems. For example, a first processor system can be used in acquiring the 2D x-ray projections. A second processor system can be used in generating the SDRR 328. A third processor system can be used to register the SDRR 328 and the selected x-ray projections including the fiducial image data. Also, a further processor system can be used in the navigation procedure to determine and illustrate the location of the instrument relative to the image data. It will be understood that all of the processor systems can be separate physical systems or can be executable programs executed by a single or less than for computer processors. A single computer processor may be used for efficient transport of a single system, while multiple computer processors may be used for modularity and speed of the various processing steps separately and at different times.

Figure 14:
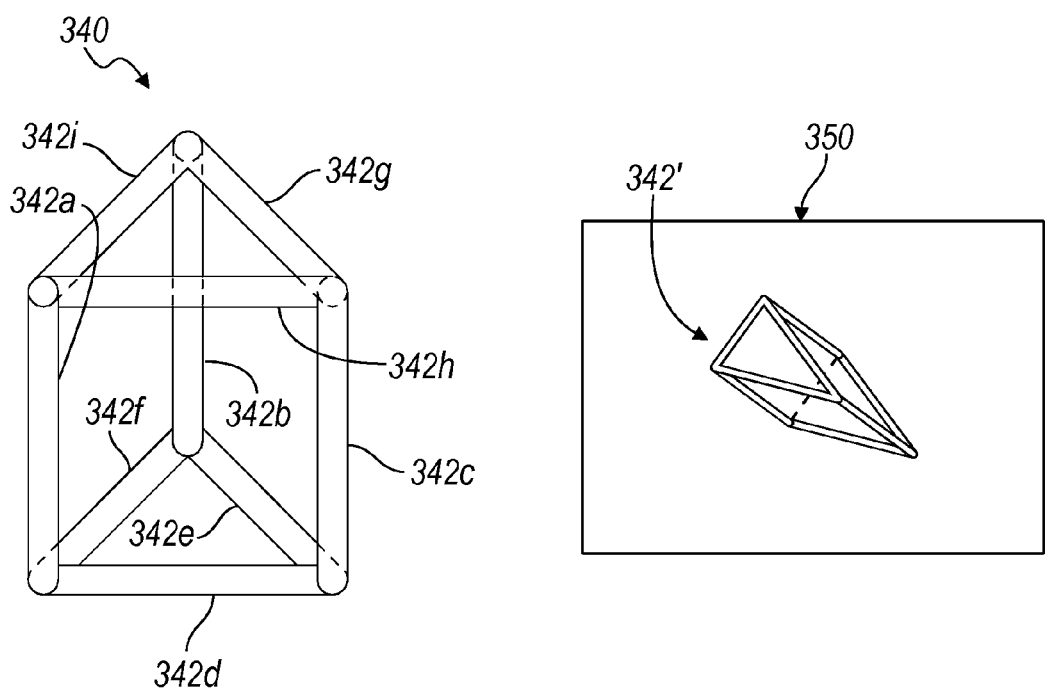
FIG. 14 is a schematic illustration of a fiducial assembly and related fiducial feature positions, according to various embodiments.

With reference to FIG. 14, a fiducial assembly 340 is schematically illustrated. It will be understood that the fiducial assembly 340 can also represent a three dimensional model of the fiducial assembly 340. The fiducial assembly 340, and its corresponding model, includes dimensions, spatial positions, and other three dimensional and two dimensional positions of various imageable fiducial portions 342a-342i. As illustrated in FIG. 14, the fiducial assembly 340 includes a plurality of rods or bars 342a-342i that are positioned in a selected configuration. An exemplarily embodiment illustrated in FIG. 14, the plurality of imageable fiducial bars 342a-342i are positioned in two substantially equilateral triangles that are connected to each other at equal distances at each of the points or apexes of the respective triangles. Accordingly, the fiducial assembly 340 includes a total of nine individual bars that can represent at least nine individual fiducial portions 342a-342i. It will be understood, however, that the bars or legs of the illustrated fiducial assembly could be radiolucent and that beads or balls of radio opaque material could instead be present at the apexes of the triangle such that a plurality of spheres or circles are present in an image.

In the fiducial assembly 340 any portion can be a fiducial feature. A combination of the bars 342a-342i can be a fiducial feature. For example, a triangle can be a fiducial feature that can be identified in the image and determined from the model of the assembly.

It will also be understood that the fiducial assembly 340 can be provided in configurations other than that illustrated, such as a different two or three dimensional configurations, than the fiducial assembly 100 discussed above, or the triangles illustrated in the assembly 340. Fiducial assemblies can include a continuous rod that intersects a plane and is curved. Fiducial assemblies can also include circles, solid geometric shapes, etc.

A determined orientation and position of each of the imageable fiducial portions can be determined in a fiducial feature layout 350. While the fiducial feature layout 350 can be determined by generating an SDRR, such as the SDRR 328 discussed above, it will be understood that the fiducial feature layout 350 need not be based upon synthetic digitally reconstructed radiographs. Rather, the fiducial feature layout 350 can be determined based on the known locations of the various imageable fiducial portions 342a-342i in a fiducial feature configuration 342' based upon the imaging system characteristics as discussed above. In other words, the known locations of the various fiducial portions 342a-342i and the known or recalled imaging system characteristics can be used to determine the fiducial feature positions 342' in the fiducial feature layout 350. The fiducial feature layout 342' is then based upon the characteristics and the known spatial configuration based upon the model of the fiducial assembly 340.

The fiducial assembly 340 can be used while imaging a subject, such as the patient 14 discussed above. The characteristics of the imaging device 12 can then be used to generate a guess or first determination of the layout of the fiducial portions 342a-342i. As discussed above, the imaging device characteristics are used in determining an extraction or determination of the fiducial features positions and/or relative locations. An iterative or non-iterative (i.e. closed form) method can then be used to coordinate the extracted or determined location of the fiducial features with the image fiducial features.

For example, an iteration or plurality of iterations can be used to match or coordinate the image fiducial features in the image data to the fiducial feature layout 342' of the image fiducial features. The iterative process can be similar to that discussed above, but not be based upon the SDRR 328 of the fiducial assembly 340, or even of the fiducial assembly 100. It will be understood that generating the fiducial feature layout 350 can be based upon any appropriate fiducial assembly that has been modeled. Accordingly, the fiducial feature layout 350 can be generated to include the fiducial features of the fiducial assembly 100 using the 3D model 100' discussed above.

Alternatively, in a non-iterative or closed form method the layout of determined in the fiducial feature layout 350 can be matched or coordinated with the image data including the image fiducial features. Due to the lack of the SDRR of the fiducial features an iterative process is not necessary to match to the image data that includes the fiducial assembly with the imageable fiducial portion, according to any of the embodiments. Rather, the fiducial features are extracted and the fiducial layout is determined directly based on the imaging system characteristics and these can be matched or coordinated directly to the image fiducial portions. It will also be understood that the image fiducial portions can be identified in image data used for the 3D reconstruction or in additional or separate images or image data. The imaging system characteristics can be known and related to each other for any and all of the images acquired of the subject, including the patient 14.

It will be further understood that the fiducial assemblies can include substantially two dimensional configurations that can be imaged with the imaging system 12. Regardless, it is a model of the fiducial assembly that can be used to determine spatial positions of the imageable fiducial portions and allow for the generation of fiducial features, such as the fiducial features 340', in a fiducial layout, such as the fiducial layout 350 to be matched or coordinated with the image data.

Once the fiducial features 342 are coordinated with the image fiducial features in the image data, a registration can be made of the image space to the subject space, such as the patient space of the patient 14. The coordination of the fiducial features 342', or any of the appropriate fiducial features, to the image fiducial features allows for a coordination or a matching of the position of the fiducial assembly 340 based upon its modeled configuration to the image data acquired of the patient 14. Thus, a coordination of the fiducial feature layout 350 allows for a registration of the image space to the subject space. The registration allows a translation between the subject space and the image space to, in turn, allow an appropriate illustration of a position of an instrument, tracked with the navigation system 10, to be displayed relative to the image data, such as the patient 14 as discussed above. It will be understood, however, that the fiducial assembly, such as the fiducial assembly 100 or the fiducial assembly 340, can be provided in any appropriate configuration as long as the configuration is modeled to allow for the generation of either the SDRR 328, the fiducial feature layout 350, or other appropriate system to allow coordination of imageable fiducial portions of the fiducial assembly relative to respective fiducial features for registration. Also, this allows for the elimination of generating the SDRR 328 of the fiducial assembly and can ease computation complexity by determining the respective positions of the fiducial features 342' alone rather than generating an SDRR of the fiducial assembly, according to various embodiments.

Figure 15:
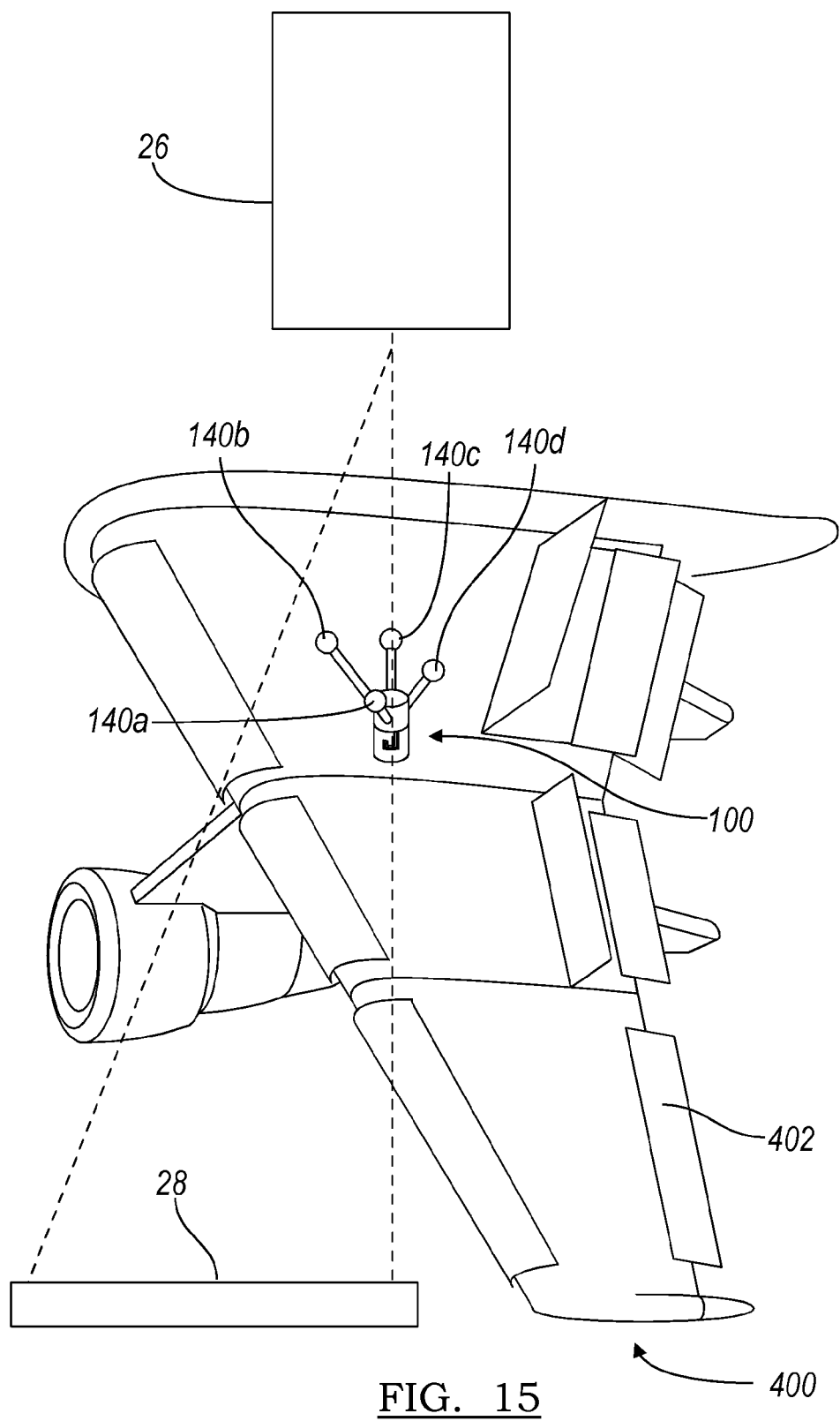
FIG. 15 is a schematic illustration of an imaging system and an imageable fiducial array is use with a selected imageable object.

With reference to FIG. 15 the fiducial assembly 100 can be attached or affixed to any appropriate subject that can include a non-human anatomy or an inanimate or non-human object. For example, the object can include an aircraft wing 400. The aircraft wing 400 can include an aileron or flap 402. The wing 400 can further include internal components not visible through the exterior surface of the wing 400. The internal components can include hydraulic or electric lines to control the aileron 402.

The imaging device 12, including the source 26 and the detector 28, can be used to image the wing 400. The surface of the wing 400 can be made of a radiolucent material, such as carbon fiber, while the internal components can be formed of radiopaque materials, such as metal. Once imaged and registered, as discussed above, a tracked instrument can be moved within the wing 400 without completely opening the wing 400 for inspection. Accordingly, one skilled in the art, will understand that the systems and methods discussed above can be used relative to any imageable object.

Figure 16A:
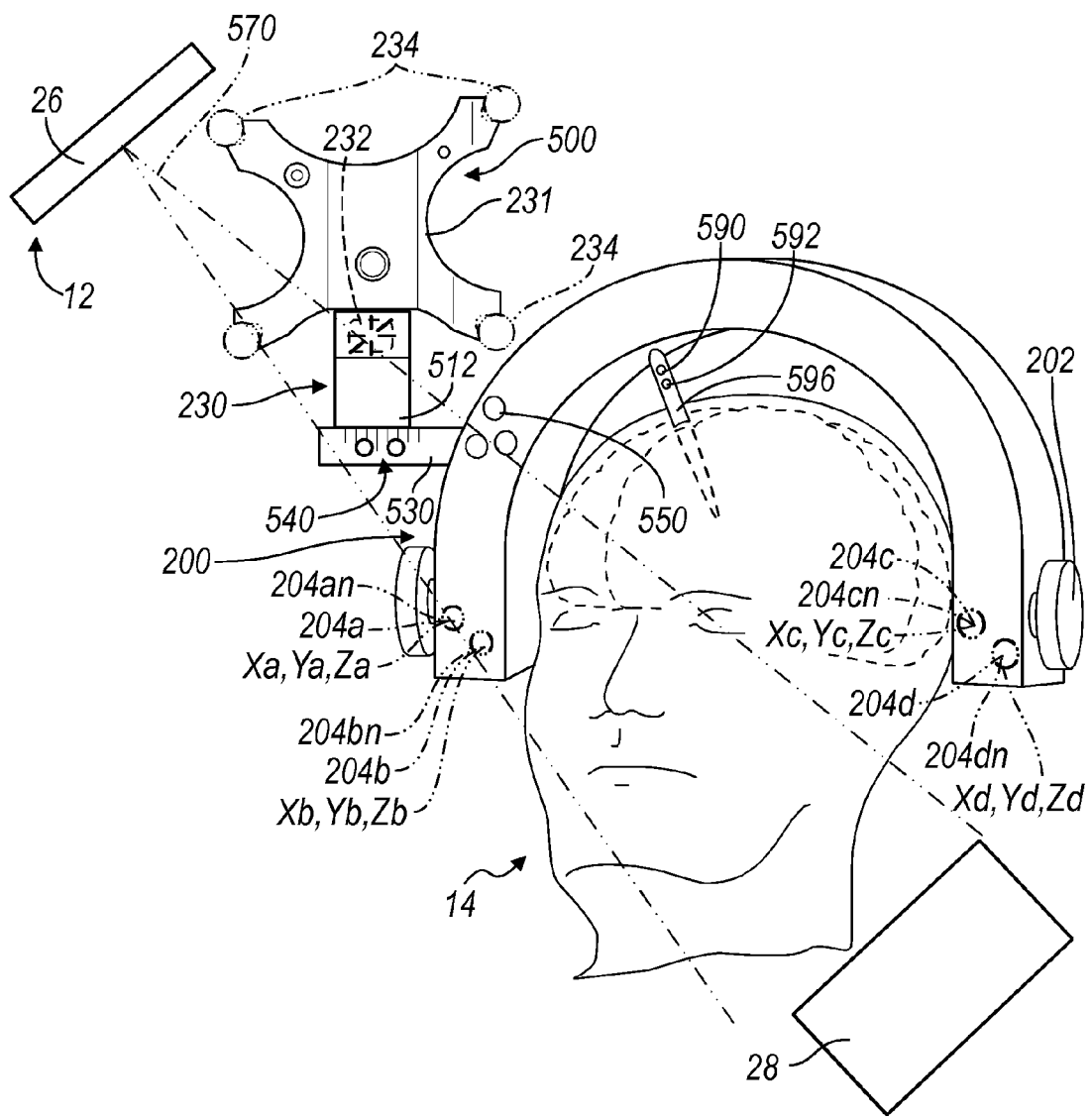
FIG. 16A is a schematic perspective view of a patient fixation device and a dynamic reference frame (DRF)
Figure 16B:
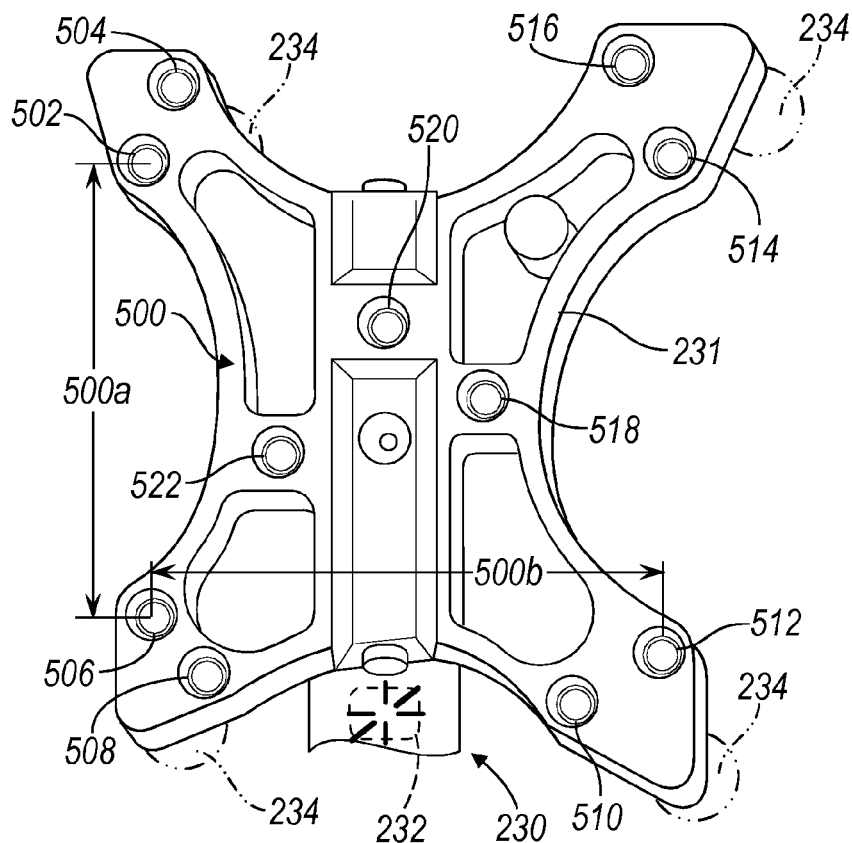
FIG. 16B is a detail view of the DRF of FIG. 16A.

According to various embodiments, as illustrated in FIG. 16A and 16B, either in combination or separate from the patient fixation device 200 can be the DRF 230. The DRF 230 can include a body portion or member 231. The DRF 230, including the member 231, can include a plurality of DRF or navigation reference frame imageable portions 500, including distinct imageable and separate imageable portions 502, 504, 506, 508, 510, 512, 514, 516, 518, 520, and 522. As discussed above, the patient fixation device 200 can include a selected number of imageable portions 204a-204d. The imageable portions 204a-204d, however, are formed into or with the patient fixation device 200. A calibration device 200 is then used to assist in determining the location of the imageable portions 204a-204d in patient or subject space. With the DRF 230 that includes the imageable portions 500 the location of the imageable portions 500 can be determined in subject space with fewer image data slices or views and in substantially only a single step, as discussed herein. In addition, the imageable portions can be positioned in closer proximity to the tracking device portion of the DRF 230. This can eliminate or reduce the need or use of the calibration device 200.

It will be understood that the imageable portions 500 can be used either separate from or together with from the imageable portions 204a-204d. Also, the imageable portions 500 can be provided in addition to or separately from the imageable portions 204a-204d. Accordingly, the imageable portions 204a-204d included with the patient holding device 200 are optional, according to various embodiments, and are not required and may be removed or at least not imaged or viewable in the acquired image data.

Figure 17:
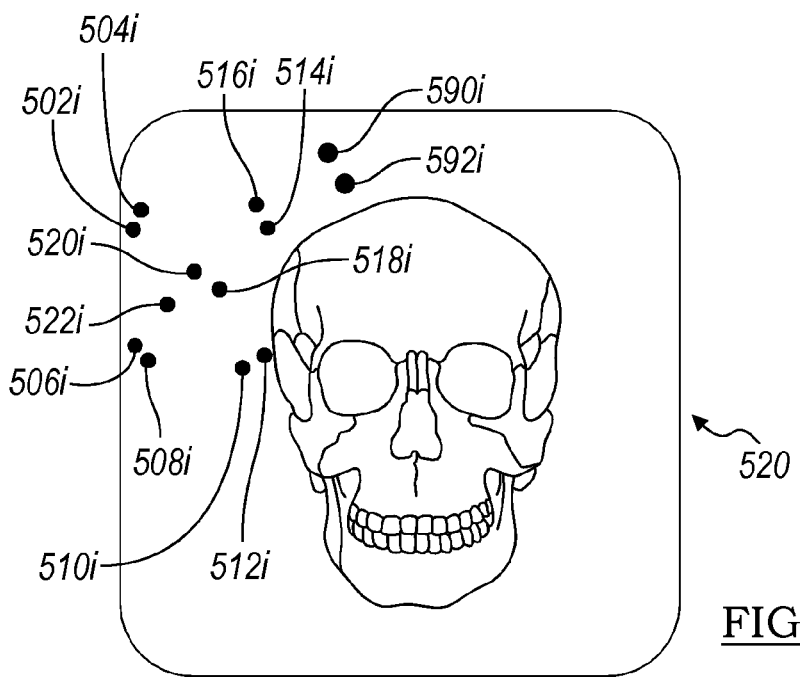
FIG. 17 is an image view of the patient and the DRF imageable portions.

With continuing reference to FIGS. 16A and 16B, each of the imageable portions 502-522 can be imaged with the imaging device 12, including those discussed above. Accordingly, the imageable portions 500 can also include respective imageable portions volumes, surfaces, and/or centers that can be viewed on an image of the patient 520, illustrated in FIG. 17. The imageable portions 500 can appear as image fiducial points 502i-522i in image data that is used to generated the image 520. It will be understood that other portions can also appear in the image 520 and that the patient fixation device 200 may or may not be opaque in the image 520.

Registration of a subject or physical space, defined by the patient 14, and image space, defined by the image 520, as discussed above, can be achieved with use of the fiducial points 502i-522i. The fiducial points 502i-522i can be identified in the image data 520 using appropriate techniques, such as manual identification or automatic identification. An automatic identification can occur by execution of instructions with a processor system, such as the navigation processor system 72. The processor system 72 can identify the fiducial points 502i-522i in the image data that generates the image 520. The fiducial points identified at the image 520 can be used to register the image space to the subject space.

The subject space is also generally defined relative to the subject 14 to which the patient fixation device 200 is affixed. The DRF 230, including the imageable portions 500, is connected to the patient fixation device 200 in a known manner. The imageable portions 500 are also at known positions (e.g. in a specific geometry as discussed herein) relative to the patient fixation device 200 and therefore the patient 14. Accordingly, after identifying the image fiducial points 502i-522i registration can occur between the image data 520 and the imageable portions 500 that are a part of the DRF 230.

The imageable portions 500 can be integrated into any portion of the DRF 230. For example, the imageable portions 500 can include radiopaque members, such as radiopaque spheres, that can be fixed within the DRF 230 and/or a post extending from the DRF 230. This can allow the DRF 230 to be connected to the patient fixation device 200 and used along and entirely for the registration process. This is opposed to the patient fixation device 200 including the imageable portions 204-204d where the imageable portions are positioned on multiple sides of the patient 14, the DRF 230 is positioned at one location relative to the patient 14 during an imaging process. Accordingly, only a single portion or limited number of views of the patient 14 need be imaged to image all of the imageable portions 500 in the DRF 230.

The imageable portions 500, including the individual portions 502-522 can be imaged in the image data. According to various embodiments, only a selected number, also referred to as a critical number, of the imageable portions 500 need be imaged and/or identifiable in the image data for an appropriate registration. That is, although 11 imageable portions 502-522 are illustrated, less than all of these (i.e. only the critical number) need be imaged and/or appear in the image 520 for registration.

In one example, the imageable six imageable portions, including 502-508, 520, and 522 can be imaged and appear as image fiducial points 502i-508i, 520i, and 522i in the image 520 or be identified in the image data for registration to a selected degree of accuracy. Thus, certain numbers (including positions and geometrical configurations) of the imageable portions 500 need not be imaged in the image data for appropriate registration. This can allow the imaging device 12 greater flexibility when imaging the subject 14 by not requiring the imaging device 12 to be moved to image the entire patient fixation device 200. That is, a fewer number of images or projections may be necessary to acquire enough image data for the registration. It can be selected, for example, that the minimum number, however, be in a selected geometry, such as spaced at least a selected distance apart or define a selected geometry in the image data.

Requiring or allowing that fewer than all of the imageable portions need be imaged can, therefore, allow a view of the DRF 230 that need not be an entire view of the DRF 230 can still allow acquisition of an appropriate amount of image data of the DRF 230, including the imageable portions 500, to allow for a registration. Moreover, it may be possible to acquire an image or image data of the critical number of the imageable portions with only a single image projection. This single projection may also be enough image data of the patient 14. Regardless, less than the entire patient holding device 200 need be imaged to allow for registration with the imageable portions 500 in the DRF 230.

The critical number can be defined in various manners. In a first example, the critical number, which can selectively include a selected geometry and/or spacing of the imageable portions 500, can be predetermined and stored in a memory system. For example, the critical number can include six of the imageable portions 500 and further require that at least two of the imaged imageable portions 500 be of the center imageable portions 518, 520, or 522. Thus, instructions can be executed by the processor, such as the processor system 72, to identify that the critical number is present in the image data or a user can identify and confirm the critical number in the image data. This may also make it efficient for a scout of initial image acquired by a user to ensure that the selected image path will acquire the critical number of the imageable portions 500. In a second example, alternatively, or in addition to a predetermined critical number, instructions can be executed by the processor to determine if the images imageable portions 500 meet predetermined and/or necessary geometry and/or spacing requirements to ensure a selected accuracy of the registration. Thus, the critical number can be determined in real time while acquiring the image data. A real time critical number determination and registration may be useful if the imageable portions are not fixed to the DRF 230, but are placed on the patient randomly.

Also, the size of the DRF 230 including the imageable portions 500 can be substantially compact. For example, the DRF 230 can be about 8 centimeters (cm)×about 8 cm, being about 64 square centimeters ($cm^2$). Thus, the compact size can assist in limiting the number of projections or size of the field of view of the imaging device necessary for image acquisition and registration.

In addition to the imageable portions 500, discussed above, the fixation portion 200 and/or a connection arm 530 that interconnects with the DRF 230 can include one or more position imageable portions 540 or 550, respectively. The imageable portions 540, 550 can include one or more imageable spheres or members that can be imaged similarly (e.g. with the same imaging modality, such as MRI or x-ray) to the imageable portions 500 associated directly or integrally with the DRF 230. The imageable portions 540, 550 can be adjacent or spaced apart from the DRF 230 having the imageable portions 500. It can be selected, however, to minimize the volume or field of view to be imaged as the imageable portions 540 and 550 can be positioned near the imageable portions 500. Also, the DRF 230 can be moved relative to the patient fixation device 200, at least initially, by the arm 530.

The imageable portions 540, 550 can be used in combination with the imageable portions 500, or at least a selected number of the imageable portions 500, to ensure that the DRF 230 is interconnected with the patient fixation device 200 in a preselected manner (e.g. location (including orientation and position) and spacing). The DRF 230 can be interconnected with the patient fixation portion 200 at a selected time during a procedure. Accordingly, the DRF 230 can be removed and replaced with the patient fixation portion 200 either preoperatively, intraoperatively, or post-operatively. Additionally, the DRF 230 can be used for multiple patients by allowing it to be removed from the patient fixation portion 200 and replaced thereto for subsequent procedures. Accordingly, the DRF 230 can be or may be required to be verified to be at a selected location relative to the patient fixation device 200. Additionally, the DRF 230 either alone or in combination with the calibration device 220 can be used to calibrate the patient fixation device 200 relative to the image data, such as the image data 520. By imaging the imageable portions 500 in the DRF and the image portions 540, 550 on the arm 530 and/or the patient fixation device 200, the location of the DRF 230 relative to the patient fixation device 200 can be determined and verified.

To assist in assuring a repeated and/or pre-selected orientation of the DRF 230 relative to the arm 530, the imageable portions 500 can include a known or selected geometric configuration relative to the imageable portions 540, 550 associated with the patient fixation device 200 or the attachment arm 530. The geometry of the imageable portions 500 relative to the imageable portions 540 or 550, or both, can be predetermined or stored for access during a procedure. Accordingly, once the DRF 230 is interconnected with the patient fixation device 500, either directly or through the fixation arm 530, the image data that is acquired can be checked to determine the geometry of the imageable portions 500 relative to the imageable portions 540 and/or 550. Thus, the orientation, location, and other attachment features of the DRF 230 can be recognized or confirmed relative to the patient fixation device 200. Thus, the image data acquired of the imageable portions 500 relative to the imageable portions 540 and/or 550 can be used to confirm or identify the location and orientation of the DRF 230 relative to the patient fixation device 200 and/or patient 14.

Additionally, the imageable portions 500, 540, and 550 are positioned relatively near each other, as illustrated in FIG. 16. Accordingly, a single image can acquire a plurality of the imageable portions 500, 540, 550. For example, as illustrated in FIG. 16, the x-ray or imaging system 12 can include the source 26 and the detector 28 where a single cone 576 of imageable energy, such as x-ray energy, can be used to acquire image data of most or substantially all of the imageable portions 500, 540 and 550. The imaging device 12 can also be moved relative to the patient 14 to ensure that appropriate image data is acquired of the patient 14 and the imageable portions 500, 540, 550. Thus, the proximity of the imageable portions 500, 540 and 550 can allow for ease of data acquisition of all or substantially all of the imageable portions in a single data acquisition or without moving the imaging system 12 a selected distance or any distance. For example, movement of less than one or two degrees, millimeters, or centimeters can ensure acquisition of image data of all of the imageable portions. Thus, the image acquisition of the critical number of the imageable portions 500 can be efficient and fast and require minimal or no movement of the imaging device 12.

The imageable portions 500 can also be provided in a unique geometry, including unique and distinct spacing and positions relative to one another. For example, a distance 500a can be between imageable portions 502 and 506. A second distance 500b can be formed between imageable portions 506 and 512. It is further understood that unique distances can be formed between each of the imageable portions 500. The unique distances can be two dimensional and three dimensional distances between each of the imageable portions 500. The unique distances form a unique geometry defined by the imageable portions 500 or any subset of the imageable portions 500 that would form the critical number of imageable portions. The geometries between each of the imageable portions can be saved in a memory system, such as one of the navigation system or imaging system discussed above. The unique geometry can be used to identify the specific imageable portions and the DRF 230. Also, the geometries can be used to identify a location of the DRF 230 relative to the tracking device 232 for registration of the subject space to the image space.

Also, the unique geometries can allow for registration of the image space to the patient space with less than all of the imageable portions 500 being identified in the image data. For example, a selected minimum or critical number of about three or at least a portion of three of the imageable portions 500 can be identified in the image data. Due to the known unique and specific geometry of the imageable portions 500, only these three imageable portions can be used to identify or form a registration as these three will have a unique geometry and their position on the DRF 230 can be known or recalled from the memory.

Also, a unique geometry and distances can be formed between the imageable portions 500 and the tracking device 232 and the imageable portions 540 and the imageable portions 550 on either the attachment arm 530 or the patient fixation device 200. Accordingly, the imageable portions 500, 540, 550 can be used to identify the specific features or configuration of the tracking device 232 relative to the patient 14 who is fixed to the patient fixation device 200. This known configuration allows for registration when less than all of the imageable portions 500, 540, 550 are identified in the image data.

In addition, the unique geometry of the imageable portions 500 within the tracking device 230 can allow for identification of the tracking device 230 in the image data. Again, a specific geometry or arrangement of the imageable portions, including some of all of the imageable portions 500, 540, 550, can be saved in a storage system and accessed during a procedure. Various geometries of groups of the imageable portions 500 that can be saved in the storage device for different and specific DRFs. For example, a spinal fixation DRF, a cranial DRF, etc. Accordingly, after the imageable portions are identified in the image data, the processor system, including the navigation system 72, can automatically identify the type of DRF based on the specific geometry identified. This, in turn, can allow for an automatic modification of a workflow for the processor system 72. For example, if a cranial DRF is identified, the processor system can immediately attempt to identify cranial or brain features, alter workflow queries related to a brain procedure, etc.

Although, the identification of the imageable portions in the image 520 can also be assisted manually (e.g. a user identifying a region that may include the image portion points 502i-522i) or performed manually (i.e. a user manually identifies each of the points). The features of the DRF 230 can then be recalled from the memory or storage device. Accordingly, the type or configuration of the DRF 230, which can include the tracking device 232, can be automatically recalled from the storage system without requiring further user input. Thus, it is understood, that the identification of the DRF 230 and the location of the tracking device 232 can also be completely automatic after acquisition of the image data and identification of the imageable portions in the image data 520. Thus, the identification of the DRF 230, the imageable portions 500 in the image data, and registration can all be substantially automatic and performed without user input once the image data is acquired.

The imageable portions 500, being in a specific or identifiable geometry, can also be used to specifically identify a surgical instrument or tracking device being used. For example, a specific and different the DRF 230 can be used for specific procedure, such as a brain stimulation implantation procedure. It is understood, however, that other tracking devices can be connected to the patient 14 for other procedures, such as a spinal procedure, an orthopedic procedure, or other procedures. Thus, the navigation system 72 or imaging system 12, which can automatically identify the specific DRF 230, can also automatically perform certain functions based upon the identification of the tracking device. For example, intra-operative workflows, as mentioned above, can be augmented within the tracking or navigation system to assist in efficiency of a procedure. For example, for a spinal procedure identifying neurological regions in a brain of a patient is generally not necessary. Thus, querying whether such regions need be identified or attempting to identify them in image data can be removed from a workflow due to an automatic identification of a tracking device based upon the unique configuration of the imageable portions.

The imageable portions 500 can also be used to identify or determine patient movement intra-operatively. For example, image data can be acquired of the patient 14 at a plurality of times during an operative procedure. During the plurality of image acquisitions, which can be spaced apart over time and sometimes can be spaced several minutes or hours apart, can be compared to one another. Due to the position of the imageable portions 500 relative to the patient holding device 200 and/or the patient 14, a determination of possible or probable, movement of the patient 14 can be made. The imageable portions 500 can be automatically identified in the later acquired image data for comparison to the previously acquired image data. The determination of the position of the imageable portions of the patient 14, can be used to determine whether the patient has moved relative to the tracking device and/or the patient holding device 230. Position of the patient can be identified with various techniques including the identification of patient surfaces and features as is generally used in the StealthStation® navigation system sold by Medtronic Navigation, Inc. having a place of business in Colorado, USA.

In addition to providing the imageable portions 500 on the DRF 230, imageable portions 540 on the attachment arm 530, and imageable portions 550 on the patient holding device 200, imageable portions can also be provided in and/or on other instruments. For example, imageable portions 590 can be provided in an instrument 596. The instrument 596 can also include other tracking devices, such as electromagnetic tracking devices, but the imageable portions 590 and 592 can also be used to identify a position of the instrument 596 directly in the image 520. Even if the instrument 596 is radiolucent, the imageable portions 590 and 592 can be identified as imageable or image features 590i and 592i in the image 520. Accordingly, the instrument 596 and its position and orientation can be identified in the image data 520. Again, it is understood that the imageable portions 590 and 592 can be provided in any appropriate number in the device 596. The number and geometry can be used to identify the specific instrument 596 for viewing and identification of locations of various portions of the instrument 596, such as a tip thereof. The geometry of the imageable portions and/or number can also be used to identify an orientation of the instrument 596 in the image 520. Again, automatic identification of the image features 590i, 592i can be used to automatically identify the instrument 596 and assist in efficiency and workflow of the procedure in addition to illustrating a location, including a position orientation, of the instrument 596.

Figure 18:
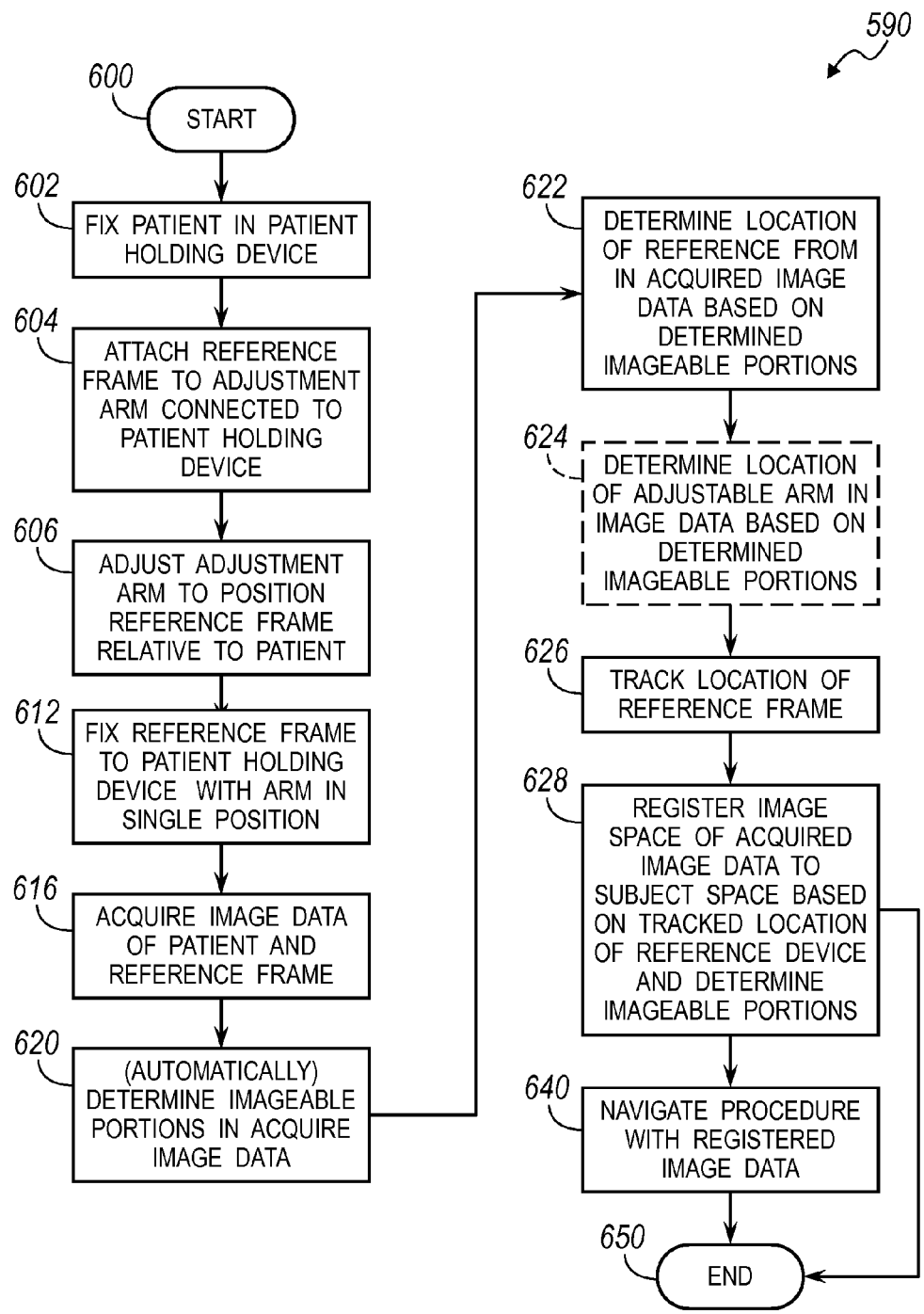
FIG. 18 is a flowchart of the method of use of the DRF with imageable portions.

The DRF 230 including the imageable portions 500 can be used for a procedure, such as to register image space acquired with the imaging system 12. The DRF 230 can also include the tracking portions 234 and 232 that can be interconnected with the patient holding device 200, as discussed above. A method 590 illustrated in FIG. 18 illustrates a method of using the DRF 230 including the imageable portions 500. Generally the method 590 can begin in start block 600 and include fixing the patient in the patient fixation device 200 in block 602. The reference device 230 can be attached to an adjustable arm connected to the patient holding device in block 604.

As discussed above, the attachment arm 530 can interconnect the reference device with the patient holding device 200 in an adjustable manner. Accordingly, the reference device 230 can be moved relative to the patient holding device 200 via the adjustable arm 530 in block 606. This can assist in assuring that the DRF 230, including the imageable portions 500, are positioned at a selected location relative to the patient fixation device 200. Additionally, because the imageable portions 500 are imaged with the imaging device, the adjustable arm 530 can assist in allowing a user, such as the physician 81, in adjusting or moving the reference device 230 including the imageable portions 500 relative to the patient 14 during the image acquisition and during a procedure. For example, the user 81 can move the DRF 230 as near as possible or in any selected proximity to a region of interest to be imaged.

It is understood that the patient 14, or any subject that is imaged can define a subject space that can include a three dimensional physical space and location. Image data acquired with the imaging device 12, or any appropriate image device can define image space that can also include three dimensions. The image data that is acquired with the imaging device 12 can be registered relative to the subject space, such as space defined by the patient 14, as generally known in the art and discussed above.

The DRF 230 can then be fixed in a single location relative to the patient holding device in block 612. As discussed above, the adjustment arm 530 can be used to adjust the location of the reference device relative to the patient holding device 200. However, for image acquisition and performing a procedure, as discussed herein especially for registration, the DRF 230 can be fixed relative to the patient fixation device 230 during acquisition of image data and after acquisition of image data for registration and navigation of a procedure. It will also be understood that the subject 14 need not be a patient, in particular a human, but can be any appropriate animal (e.g. canine) or it can be an inanimate object that internal components can be appropriately imaged, including a computer system, and/or other subjects. Nevertheless, once the reference frame is fixed at the selected single location relative to the patient fixation device 200 in block 612, image data can be acquired in block 616.

Image data is acquired of the patient 14 and the imageable portions 500 of the reference device. The image data acquired can generally include at least 50% of the DRF 230 or any appropriate portion of the DRF 230 that allows for image data to be acquired of the selected critical number of the imageable portions 500. An appropriate number of the imageable portions can be selected by a user, automatically, or generally by the system. The number of imageable portions to be acquired of the image data can generally relate to the number desired or required for an appropriate registration of the image data to the patient. For example, three of the imageable portions 500 can be imaged for an appropriate registration. More or less can be imaged based upon the geometry of the imageable portions, and a desired accuracy of the registration.

The imageable portions can be determined in the image data in block 620. The imageable portions can be identified substantially automatically or with minimal user input. For example, substantially after acquisition of the image data, the processing system, including the processing system 72, can execute appropriate instructions to search the image data for the imageable portions 500. The imageable portions 500 can be identified by the processor system 72 by shape, configuration (such as density), a specific geometry of the specific imageable portions (e.g. spherical, pyramid, or the like) or other automatic identification procedures. Additionally, or in combination therewith, a user can identify the imageable portions at a selected time or based upon a prompt from the navigation system 72. Accordingly, the image data can be displayed for the user 81 on the display device 74 and the user 81, or any appropriate user, can identify the imageable portions in the image 520. Alternatively, or in addition thereto, the processor system 72 in executing selected instructions can request that the user select the action such as identifying the imageable portions in the image data.

After the imageable portions are identified in block 620, a location of the DRF 230 in the image data can be determined based on the determined imageable portions in block 622. As discussed above, the DRF 230 including the imageable portions 500 can include them arranged in a selected geometric configuration on portions of the DRF 230. Accordingly, after the imageable portions are identified in block 620, the location of the DRF 230 can be determined and identified in the image data based upon the geometric location of the imageable portions in the image data.

In addition, as discussed above, imageable portions can be included on the patient fixation device 200 as the imageable portions 550 and imageable portions 540 can be included on the adjustable arm 530. Accordingly, the processor system 72 can also identify each of the other elements and their locations, including the adjustable arm 530 and the patient fixation device 200, in addition to the location of the reference frame 234 in the image data. Again, the determination can be substantially automatic after determining the imageable portions of the image data. Alternatively, the image data can be displayed to the user 81 and the user 81 can identify the various portions (e.g. with a touch screen, moving a cursor on a display device, etc.). Alternatively, or in addition thereto, the user 81 can order or command the processor system 72 to identify the various portions, including the DRF 230, based upon the determined imageable portions. It will be understood, however, that the determined location of the adjustment arm in block 624 and any other portion in the image data can be purely optional. Registration of the image space to subject space can be based on a selected element, such as a determination of the location of the reference frame alone and the imageable portions 500 associated therewith.

The location of the DRF 230 can be tracked in block 626. As discussed above, the DRF 230 can include a tracking feature or device such as an electromagnetic tracking device 232, an optical tracking device 234, or other appropriate tracking device. The position of the tracking device relative to the imageable portions 500 in the subject space is known and saved to be accessed by the processor system 72. For example, a database of various reference frames can be saved that is accessed by the processor system 72 to allow the processor system 72 to identify the position of the tracking device relative to the imageable portions 500. Not only can the processor system 72 automatically identify the specific reference frame being imaged, but also a location of the tracking device relative to the imageable portions without input by the user 81 as the identification based on a saved geometry can be accessed from a database, such as one stored in a storage system. Alternatively, or in addition thereto, the location of the tracking device can be input by the user 81.

Based upon the tracked location of the tracking device and the known location of the tracking device relative to the imageable portions in the DRF 230, and the determined location of the imageable portions from block 620, a registration of the image space to the subject space can be performed in block 628. Registration of the image space to the subject space can be done substantially automatically based on the tracked location of the tracking device in the subject space and the determined location of the imageable portions in the image space, and the known location between the tracking device. The registration based on these known locations and features is generally understood in the art. Moreover, this can be a substantially single step in a process, where image data is loaded and the processor system 72 performs a registration. That is, the identification of the imageable portions, determining or recalling a location of the tracking device relative to the imageable portions on the DRF 230, etc. is all performed without user intervention and as a single step in a process.

After the registration has occurred, the method can then allow for a navigated procedure to occur using the registered image data in block 640. An instrument, such as the instrument 596, can be used to perform the procedure. As discussed above, the instrument 596 can include imageable portions 590, 592 to assist in tracking the instrument 596. Accordingly, the instrument 596 can be tracked relative to the registered image data. It is understood, however, that a different tracking device can also be used to track the instrument 596 relative to the patient 14 based upon the registered image data, where a tracking system tracks the instrument and an icon representing the instrument is super-imposed on the image 520.

It will be understood, however, that navigating a procedure is not required. Therefore, the method can end in block 650 after the registration has occurred in block 628. Alternatively, the procedure 590 can end in block 650 after navigating the procedure in block 640. The navigated procedure can include any appropriate additional steps, including those understood in the art, including performing a procedure (e.g. deep brain stimulation) and related procedure steps such as creating bore hole in a patient 14, positioning and fixing the deep brain stimulation probe, and other selected portions of the procedure.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A navigation system, comprising:
a patient holding device configured to hold a patient fixed in a substantially single holding position relative to an imaging device during acquisition of image data of the patient;
a navigation reference frame removably fixed to the patient holding device to remain in a substantially single reference frame position relative to the patient during the image data acquisition and a procedure on the patient;
a plurality of navigation reference frame imageable portions included with the navigation reference frame and viewable in acquired image data of the patient when the plurality of navigation reference frame imageable portions are in a field of view of the imaging device;
a tracking device included with the navigation reference frame operable to be tracked and at a known location relative to the plurality of navigation reference frame imageable portions; and
a navigation processor system configurable to execute instructions to determine a location of the plurality of navigation reference frame imageable portions in the acquired image data, determine a subject space location of the tracking device, and register the acquired image data to the subject space based at least on the acquired image data of the plurality of navigation reference frame imageable portions.

2. The navigation system of claim 1, wherein the navigation frame is connected to the patient holding device with a reference frame holding arm that extends from the patient holding device.

3. The navigation system of claim 2, further comprising:
a reference frame holding arm imageable portion.

4. The navigation system of claim 3, wherein the reference frame holding arm imageable portion includes a plurality of reference frame holding arm imageable portions that are arranged in a selected and specific geometric formation.

5. The navigation system of claim 1, further comprising:
a localizer with a tracking system operable to track in subject space the tracking device.

6. The navigation system of claim 5, wherein the localizer is at least one of an electromagnetic localizer or an optical localizer.

7. The navigation system of claim 1, further comprising:
an instrument having a plurality of instrument imageable portions;
wherein the plurality of instrument imageable portions and the plurality of navigation reference frame imageable portions are imageable with a single imaging modality.

8. The navigation system of claim 1, wherein the plurality of navigation reference frame imageable portions are set in a specific geometry within the navigation reference frame so that the specific geometry is operable to be identified in a single projection of the acquired image data including the navigation reference frame.

9. The navigation system of claim 1, further comprising:
a plurality of patient holding device imageable portions fixed to the patient holding device;
wherein the plurality of patient holding device imageable portions and the plurality of navigation reference frame imageable portions are imageable with a single imaging modality;
wherein the navigation processor system is further configurable to execute instructions to determine a location of the plurality of navigation reference frame imageable portions in the acquired image data relative to the plurality of patient holding device imageable portions to determine a position of the patient holding device relative to the navigation reference frame.

10. A navigation system, comprising:
a subject holding device configured to hold a patient fixed in a substantially single holding position relative to an imaging device during acquisition of image data of the subject;
a navigation reference frame removably fixed to the subject holding device to remain in a substantially single reference frame position relative to the subject during the image data acquisition and a procedure on the subject;
a plurality of navigation reference frame imageable portions included with navigation reference frame and viewable in acquired image data of the patient when the plurality of navigation reference frame imageable portions are in a field of view of the imaging device, wherein the plurality of navigation reference frame imageable portions are set in the of navigation reference frame to have a selected and identifiable geometry in the acquired image data;
a tracking device fixed to the navigation reference at a known location relative to the plurality of navigation reference frame imageable portions, wherein the tracking device is operable to be tracked in subject space;
a navigation processor system configurable to execute instructions to determine a location of the plurality of navigation reference frame imageable portions in the acquired image data, determine a subject space location of the tracking device, and register an image space of the acquired image data to the subject space based at least on the acquired image data of the plurality of navigation reference frame imageable portions; and
a display device configured to display the image data defining an image space that is registered to the subject space.

11. The navigation system of claim 10, wherein the navigation processor is configured to execute instructions to determine a configuration of the navigation reference frame when a critical number, but less than all of the plurality of navigation reference frame imageable portions, are identified in the acquired image data.

12. The navigation system of claim 10, wherein the navigation processor is configured to execute instructions to register the subject space to the image space when a critical number, but less than all of the plurality of navigation reference frame imageable portions, are identified in the acquired image data.

13. The navigation system of claim 12, wherein the critical number is three.

14. The navigation system of claim 10, wherein the plurality of navigation reference frame imageable portions are set in a specific geometry within the navigation reference frame so that the specific geometry is operable to be identified in the acquired image data of the navigation reference frame.

15. The navigation system of claim 14, further comprising:
a plurality of patient holding device imageable portions fixed to the patient holding device;
wherein the plurality of patient holding device imageable portions and the plurality of navigation reference frame imageable portions are imageable with a single imaging modality;
wherein the navigation processor system is further configurable to execute instructions to determine a location of the plurality of navigation reference frame imageable portions in the acquired image data relative to the plurality of patient holding device imageable portions to determine a position of the patient holding device relative to the navigation reference frame.

16. The navigation system of claim 15, wherein the navigation processor system is further configurable to execute instructions to determine movement of the navigation reference frame and the patient holding device based upon a change in location between the plurality of patient holding device imageable portions and the plurality of navigation reference frame imageable portions between the acquired image data from the image data acquisition and a subsequent image data from a subsequent image data acquisition.

17. A method of registering an image space to a subject space, comprising operating a processor system to execute instructions to:
determine a subject space location of a navigation reference frame in a subject space with a tracking device;
determine a specific geometry of a plurality of navigation reference frame imageable portions in an image data;
determine an image space location of the navigation reference frame based on the determined specific geometry of the plurality of navigation frame imageable portions in the image data;
recall a location of the tracking device relative to the plurality of navigation reference frame imageable portions; and
register an image space defined by the image data and the patient space based on the determined subject space location of a navigation reference frame and the determined image space location of the navigation reference frame.

18. The method of claim 17, further comprising:
acquiring the image data that defines the image space.

19. The method of claim 17, further comprising:
manually identifying the navigation reference frame imageable portions in the image data.

20. The method of claim 17, wherein the plurality of navigation reference frame imageable portions includes less than a total number of navigation reference frame imageable portions fixed to the navigation reference frame.

21. The method of claim 17, further comprising:
acquiring the image data that defines the image space of only the plurality of navigation reference frame imageable portions that includes less than a total number of navigation reference frame imageable portions fixed to the navigation reference frame.

22. The method of claim 21, wherein the plurality of navigation reference frame imageable portions includes three navigation reference frame imageable portions.

23. The method of claim 17, further comprising:
acquiring a first image data set of the plurality of navigation reference frame imageable portions and patient fixation device imageable portions;
acquiring a second image data set at a time different than the first image data set acquisition of the plurality of navigation reference frame imageable portions and patient fixation device imageable portions; and
operating the processor system to execute further instructions to:
compare the first image data set and the second image data set to determine a change in location of the plurality of navigation reference frame imageable portions and patient fixation device imageable portions.

* * * * *